(12) United States Patent
Madison

(10) Patent No.: US 12,053,356 B2
(45) Date of Patent: Aug. 6, 2024

(54) SELF-ATTACHING ABSORBENT WRAP

(71) Applicant: Mary G. Madison, Monroe, WA (US)

(72) Inventor: Mary G. Madison, Monroe, WA (US)

( * ) Notice: Subject to any disclaimer, the term of this patent is extended or adjusted under 35 U.S.C. 154(b) by 0 days.

(21) Appl. No.: 18/363,538

(22) Filed: Aug. 1, 2023

(65) Prior Publication Data

US 2024/0074913 A1 Mar. 7, 2024

Related U.S. Application Data

(60) Provisional application No. 63/404,038, filed on Sep. 6, 2022.

(51) Int. Cl.
| | | |
|---|---|---|
| *A61F 13/06* | (2006.01) | |
| *A61F 13/00* | (2024.01) | |
| *A61F 13/0246* | (2024.01) | |

(52) U.S. Cl.
CPC ...... *A61F 13/064* (2013.01); *A61F 13/00055* (2013.01); *A61F 13/0246* (2013.01)

(58) Field of Classification Search
CPC ............ A61F 13/06; A61F 13/064; A61F 2013/00119; A61F 2013/00102; A61F 2013/00089; A61F 13/0273; A61F 13/00004; A61F 13/0246; A61F 13/00055; A61F 13/42
See application file for complete search history.

(56) References Cited

U.S. PATENT DOCUMENTS

| | | | | |
|---|---|---|---|---|
| 7,145,053 B1 * | 12/2006 | Emenike | ................. | A61F 13/42 |
| | | | | 604/362 |
| 2014/0257154 A1 * | 9/2014 | Brown | ................. | A61H 9/0078 |
| | | | | 601/152 |

FOREIGN PATENT DOCUMENTS

| | | | | |
|---|---|---|---|---|
| FR | 2715832 A1 * | 8/1995 | .......... | A61F 13/064 |
| WO | 2012142155 A2 * | 10/2012 | | |

OTHER PUBLICATIONS medicaleshop.com; "Eclypse Boot Super Absorbent Wound Dressing"; website; located at: https://www.medicaleshop.com/eclypse-boot-super-absorbent-wound-dressing; accessed on Aug. 1, 2023.
Grayline medical.com; "Advancis Dukal Eclypse Contour Super Absorbent Wound Dressing, 12"×20""; website; located at: https://www.graylinemedical.com/products/advancis-dukal-eclypse-contour-super-absorbent-wound-dressing-12-x-20; accessed on Aug. 1, 2023.
Compression health.com; "Eclypse Foot-Super Absorbant Foot Wrap Dressing—5 per Box"; website; located at: https://compressionhealth.com/eclypse-foot-super-absorbant-foot-wrap-dressing-5-per-box/; accessed on Aug. 1, 2023.

* cited by examiner

*Primary Examiner* — Ophelia A Hawthorne
(74) *Attorney, Agent, or Firm* — Maschoff Brennan

(57) ABSTRACT

A self-attaching absorbent wrap is provided that can be easily secured and adjusted. The absorbent wrap may include a layered construction that includes an absorbent material sandwiched between a fluid impermeable outer layer and a fluid permeable inner layer.

38 Claims, 16 Drawing Sheets

SELF-ATTACHING ABSORBENT WRAP

CROSS REFERENCE TO RELATED APPLICATION

This application claims priority to U.S. Provisional Patent Application No. 63/404,038, filed on Sep. 6, 2022, which is incorporated herein by reference in its entirety.

BACKGROUND

Edema, or swelling caused by fluid trapped in tissues of the human body, is a common condition that may be caused by a number of factors. For example, edema may be caused by spending too much time sitting or standing in one place. Gravity, in these cases, may contribute to edema by pulling water and other fluids down into the lower extremities. Edema may also be caused by weakened valves of the veins. When the valves in veins are weak, it is hard for veins to push blood to the heart, which leads to varicose veins and a buildup of fluid in the legs. Edema is also a common symptom that is associated with a number of medical conditions, including heart failure and lung, liver, kidney, and thyroid diseases. Edema is also a common side effects from certain medications, including blood pressure and pain management medications. Poor nutrition, pregnancy, and a compromised immune system can also lead to edema.

In some cases, swelling caused by edema can become so severe that fluid will leak out directly from the skin. This is known as weeping edema. It is difficult to effectively and efficiently treat weeping edema and other weeping wounds (collectively referred to as weeping edema).

There are currently a number of treatments used by patients, caregivers, and health professionals to absorb and contain the fluid that leaks in cases of weeping edema. One treatment commonly used by health professionals to treat weeping edema is a layered compression wrap. Layered compression wraps, however, suffer from a number of deficiencies that make them less than ideal to treat weeping edema. First, there often exists a delay in access to compression treatment. From the time that patients start experiencing fluid leaking from their leg(s), there is often a 2 to 5 day period of time before a compression wrap treatment can be initiated. The doctor is called and an office appointment is made. The patient sees the doctor and is most commonly referred to a wound care clinic. The patient makes an appointment for the wound care clinic and is then seen. During this time, patients are forced to manage their weeping fluid by a variety of methods that are at best not ideal and at worst potentially harmful.

Second, compression treatment can be unsafe. Before compression wraps can be used, patients must have a test performed to check if the circulation to the affected extremity is adequate for this treatment to be used safely. For some patients it is not, and they are left without this option for managing the leaking fluid.

Third, compression treatment is not effective for bed-bound patients who cannot ambulate. It is therefore an expensive and inappropriate strategy to manage weeping fluid in these cases.

Fourth, compression wraps do not always resolve weeping edema and can quickly saturate with fluid and leak. Even when a compression wrap is applied, fluid can and does continue to leak from the extremity, causing the compression wrap material to become saturated. Once saturated, fluid may again leak from the wrap onto and soil clothing, furniture, bed linens etc.

Fifth, compression wraps can become too tight and painful. Fluids in the body often shift, which can cause the size of the effected extremity to enlarge in spite of a compression treatment. This can lead to a "tourniquet effect," which can reduce blood flow to the extremity, which in turn causes pain that often requires the wrap to be removed. If patients are unable to communicate and cannot verbalize this issue, the problem can go unrecognized and cause harm to the limb.

Thus, while the layered compression wrap is a commonly utilized treatment for managing the issue of weeping edema, it is not able to be used universally on all patients who develop this distressing symptom either due to inadequate circulation to the limb or because the patient is non-ambulatory and it lacks efficacy. Patients are left to self-deal with the leaking fluid during the time it takes to see their doctor and be sent to the wound clinic for assessment and treatment, and this treatment does not always work to resolve the problem. Furthermore, it can become painful and unsafe if the leg continues to enlarge and the circulation becomes dangerously compromised.

Another treatment commonly used by healthcare professionals to absorb and contain leaking fluid is to use bulky gauze wraps. But this fails to adequately meet patient needs for a number of different reasons. First, bulky gauze wraps are difficult and cumbersome to apply. Bulky gauze wraps require the application of absorbent materials such as gauze pads, abdominal pads, or even perineal pads secured with gauze rolls. This can be challenging even for the experienced healthcare professional who often struggles to hold the material in place while maneuvering the gauze roll to secure it.

Second, gauze wraps become saturated quickly. Even with the heavy use of bulky material, gauze material can become saturated quickly, depending on how heavy the weeping fluid is. Often, patients are unable to change these dressings on their own, so once again the fluid is leaking and soiling the patient and environment. For this reason, frequent visits from a healthcare professional are required to change the wraps. In some cases, home health and hospice nurses are required to see patients every 1 to 2 days to provide dressing changes. Most often, by the time the patient is seen, the wraps are soaked and often falling off the extremity due to the weight of the fluid.

Third, gauze wraps can cause a "tourniquet effect" and other types of skin stress. As noted with compression wraps, the risk of wrapping the extremity too tightly or the material becoming too tight with leg swelling is present with the use of non-compressive gauze wraps as well. Additionally, it is difficult to apply the material smoothly without wrinkles, and skin stress can occur which can cause areas of skin damage to the moist, fragile skin.

Thus, the application of bulky gauze wraps is very cumbersome and difficult to apply smoothly to the extremity and most often only provides a short-lived remedy because they saturate quickly and do not remain intact. Frequent healthcare professionals visits are required to reapply fresh dressings.

Yet another treatment commonly used to manage to absorb and contain leaking fluid falls in the category of "miscellaneous self-help remedies," which includes the use of materials commonly found in the home environment such as paper and linen towels, incontinence pads, cellophane wrap, plastic bags, or over the counter first aid supplies. These treatments also suffer from a number of disadvantages. First, cellophane wrap and plastic bags are an unsafe way to treat weeping edema. When an extremity is wrapped in non-absorbent and non-breathable material, the skin becomes severely macerated (water-logged) and very fragile. Additionally, the warm and moist environment created by these materials can entrap and proliferate the growth of bacteria which creates a risk for infection. This is not considered a safe option for managing weeping edema.

Second, bath towels/paper towels are difficult to secure around an extremity. Often, patients, friends, or family members will attempt to secure these materials to an extremity with tape to provide temporary absorption and protection. If not clean, these materials can also increase the risk of infection.

Third, incontinence pads are often only effective when sitting or lying down. These pads are placed under an extremity such as the legs to capture leaking fluid. However, if the patient needs to get up to walk, they will drip fluid onto the floor because the extremity is not covered. In addition, if used in bed, these pads will most often become displaced with movement while asleep, resulting in soiled bed linens.

Thus, while there are a variety of self-help strategies commonly used by patients in the home, none of them adequately manage weeping edema due to lack of absorbency, inability to secure properly, and/or inability to keep in place when sleeping. Additionally, there are safety issues related to increased fall risk due to fluid leaking down the leg and foot creating a slippery surface, or from material falling off while walking and creating a tripping hazard.

There exists a need for an improved absorbent wrap that is faster and requires less skill to apply. The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

In one embodiment, a self-attaching absorbent lower leg and foot wrap is disclosed. The wrap may include a lower leg portion that includes a first wing, a first connecting strip, and a first attachment mechanism. The first wing may be secured at one end to the first connecting strip and the first attachment mechanism may be self-attaching and selectively adjustable. The wrap may also include a foot portion that includes a second wing, a second connecting strip, and a second attachment mechanism. The second wing may be secured at one end to the second connecting strip and the second attachment mechanism may be self-attaching and selectively adjustable. The first wing, the second wing, the first connecting strip, and the second connecting strip may each include a layered construction comprising an absorbent material sandwiched between a fluid impermeable outer layer and a fluid permeable inner layer. The first and second connecting strips may be connected to each other to link the lower leg portion and the foot portion together. The first and second wings may be separated from each other such that they lack a direction connection.

In some embodiments, the fluid impermeable outer layer and the fluid permeable inner layer may be made from non-woven materials. In these embodiments, the fluid impermeable outer layer may be breathable.

In some embodiments, the absorbent material may include a polymer.

In some embodiments, the first and second attachment mechanisms may include hook and loop fasteners.

In some embodiments, the first and second attachment mechanisms may include an adhesive tape.

In some embodiments, the first connecting strip may include an additional layer of the absorbent material.

In some embodiments, the outer surfaces of the first wing, the second wing, the first connecting strip, and the second connecting strip may be made from a unitary piece of a non-woven material.

In some embodiments, the inner surfaces of the first wing, the second wing, the first connecting strip, and the second connecting strip may be made from a unitary piece of a non-woven material.

In some embodiments, the foot portion may further include a heel segment that lacks the layered construction. In these embodiments, the heel segment may include a single layer of an elastic material.

In some embodiments, the lower leg and foot wrap may also include a moisture indicator that provides a visual indication of the amount of liquid contained within the absorbent layer.

In some embodiments, the first and second wings may have tapered shapes such that they become more narrow as they move away from the first and second connecting strips.

In another embodiment, a self-attaching absorbent lower leg and foot wrap is disclosed. This wrap may include an elongated strip that includes a leg portion that is configured to be secured to a back of a leg and a foot portion that is configured to be secured to a bottom of a foot. This wrap may also include a first leg wing and a second leg wing connected to and separated by the leg portion of the elongated strip. The first leg wing may include a first element of a first attachment mechanism and the second leg wing may include a second element of the first attachment mechanism. This wrap may also include a first foot wing and a second foot wing connected to and separated by the foot portion of the elongated strip. The first foot wing may include a first element of a second attachment mechanism and the second foot wing may include a second element of the second attachment mechanism. The first and second attachment mechanisms may be selectively adjustable. The elongated strip, the first and second leg wings, and the first and second foot wings may include a layered construction comprising an absorbent material sandwiched between a fluid impermeable outer layer and a fluid permeable inner layer. The first and second leg wings may be separated from the first and second foot wings such that they lack a direction connection.

In yet another embodiment, a self-attaching absorbent lower leg and foot wrap is disclosed. The wrap may include a fluid permeable inner layer that includes an inner leg wing, an inner foot wing, and an inner elongated strip constructed from a single piece of non-woven material. The wrap may also include a fluid impermeable outer layer that includes an outer leg wing, an outer foot wing, and an outer elongated strip constructed from a single piece of non-woven material, wherein the inner layer and the outer layer have a substantially similar size and shape and are attached around their edges. The wrap may also include an absorbent material sandwiched between the fluid permeable inner layer and the fluid impermeable outer layer, a first self-attaching and selectively adjustable attachment mechanism that secures the inner leg wing and outer leg wing around a leg, and a second self-attaching and selectively adjustable attachment mechanism that secures the inner foot wing and outer foot wing around a foot.

The objects and/or advantages of the embodiments will be realized or achieved at least by the elements, features, and combinations particularly pointed out in the claims. It is to be understood that both the foregoing general description and the following detailed description are given as examples and explanatory and are not restrictive of the present disclosure, as claimed.

BRIEF DESCRIPTION OF THE DRAWINGS

Example embodiments will be described and explained with additional specificity and detail through the use of the accompanying drawings.

DESCRIPTION OF EMBODIMENTS

Figure 1A:
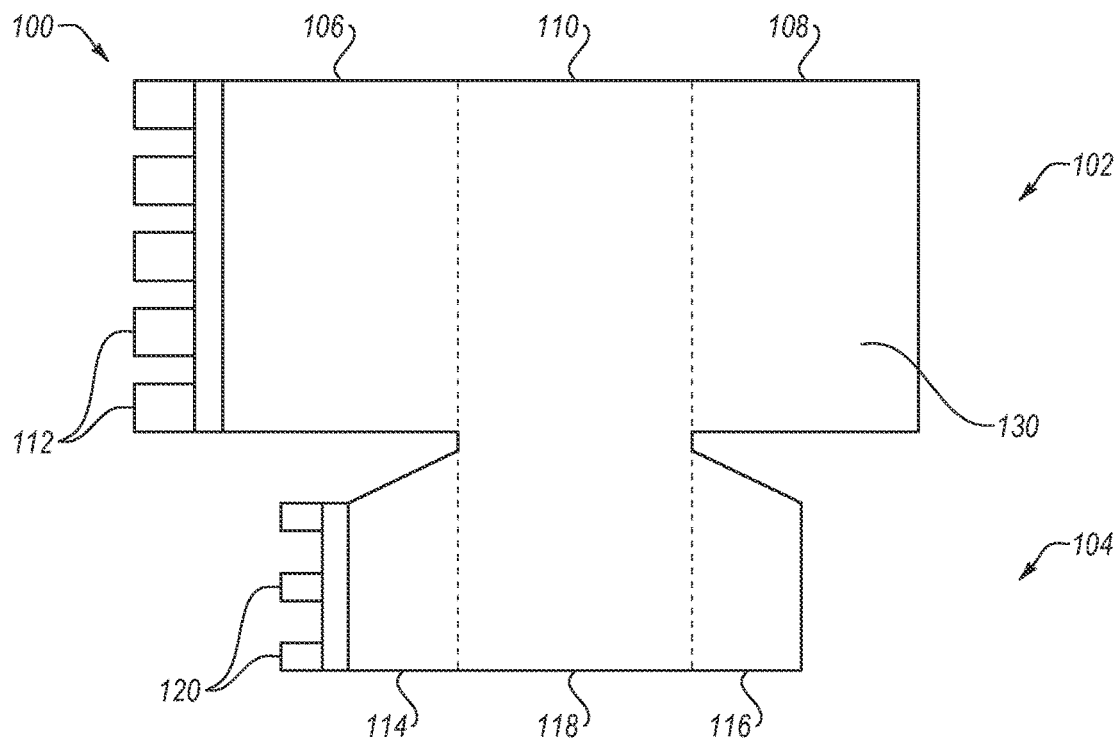
FIGS. 1A-1C illustrate a first exemplary absorbent wrap.

As provided above, there are many treatment options available for weeping edema. These treatment options include compression wraps, gauze wraps, and a variety of self-help remedies. None are ideal to treat the issue of weeping edema effectively and efficiently. An improved weeping edema treatment option is described herein to resolve disadvantages associated with current treatment options.

The absorbent wrap of the present disclosure is an improvement over each of the treatment options currently available for weeping edema, and provides a solution for effectively containing any bodily fluid including but not limited to serous fluid, fibrinous fluid, sanguineous fluid, serosanguineous fluid, haemoserous fluid, seropurulent fluid, lymphatic fluid, and any other fluid, which can drain from wounds or the surface of the skin.

One embodiment of the present disclosure provides a simple and safe absorbent wrap that can be used in the home and can be easily applied by non-healthcare professionals. In some embodiments, the absorbent wrap of the present disclosure is easy to adjust if it becomes too tight or too loose and can be changed as frequently as needed or desired. In some embodiments, the absorbent wraps of the presents disclosure can also be used in addition to compression wraps to absorb fluid and protect the environment if the compression wrap becomes saturated. In addition, the absorbent wrap may be used to bridge patients as they wait to be treated.

In some embodiments, the absorbent wrap of the present disclosure is easy to secure to the extremity and would, in many cases, eliminate the need for a healthcare professional to provide dressing changes. If a healthcare professional is still needed, the time required to secure the absorbent wrap is much less than the time required to apply a bulky gauze wrap.

In some embodiments, the absorbent wrap of the present disclosure is available without a doctor's order or prescription, and patients or their family members can buy the absorbent wrap on their own and have a clean, safe, and easy to apply alternative to use whenever needed. The absorbent wrap of the present disclosure can be used at night to keep bed linens from becoming soiled, and if the patient is able to ambulate he or she can do so with a lower risk for falls relative to any other self-help options.

The absorbent wrap of the present disclosure also provides a solution to scenarios where patients have multiple wounds in various locations on an extremity, such as a lower leg. In some embodiments, the absorbent wrap of the present disclosure is sufficiently large to cover a wide area of a patient's body and thus able to dress multiple wounds with a single wrap.

To accomplish these improvements, in some embodiments of the present disclosure, a self-attaching absorbent lower leg and foot wrap is provided that includes a lower leg portion having a first wing, a first connecting strip, and a first attachment mechanism. The first wing may be secured at one end to the first connecting strip and the first attachment mechanism may be self-attaching and selectively adjustable. The wrap may also include a foot portion that has a second wing, a second connecting strip, and a second attachment mechanism. The second wing may be secured at one end to the second connecting strip and the second attachment mechanism may be self-attaching and selectively adjustable. The first wing, the second wing, the first connecting strip, and the second connecting strip may each include a layered construction comprising an absorbent material sandwiched between a fluid impermeable outer layer and a fluid permeable inner layer. The first and second connecting strips may be connected to each other to link the lower leg portion and the foot portion together. The first and second wings may be separated from each other such that they lack a direction connection.

Figure 1B:
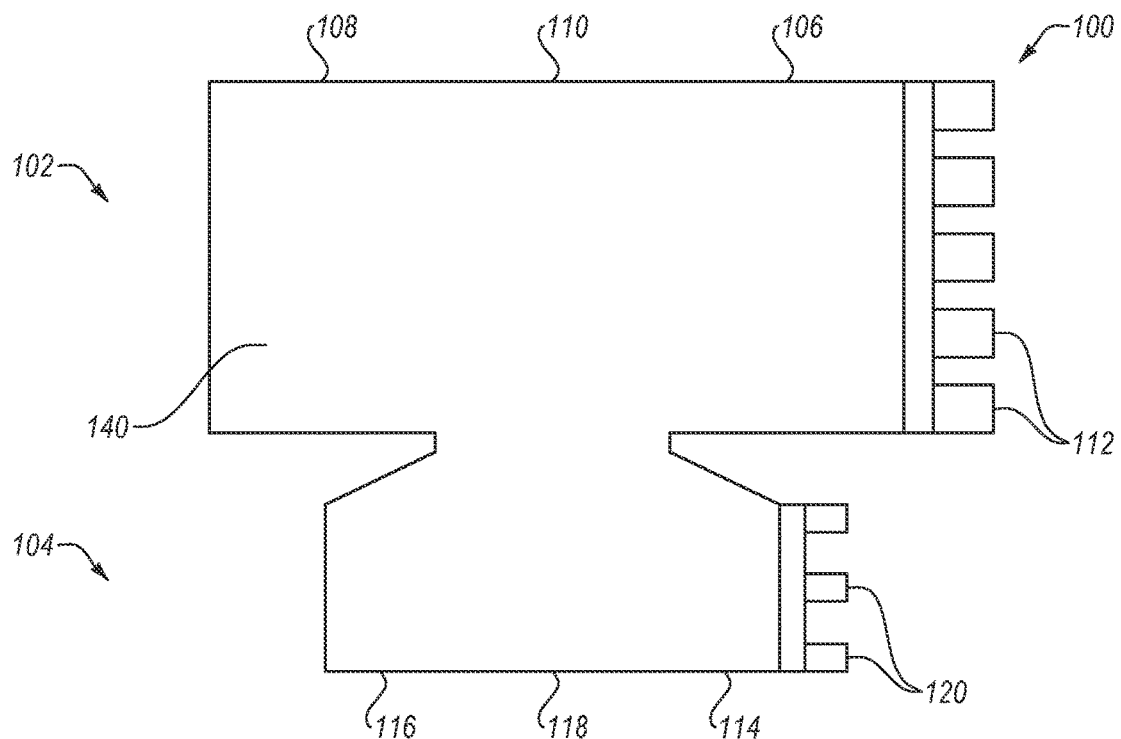
Figure 1C:
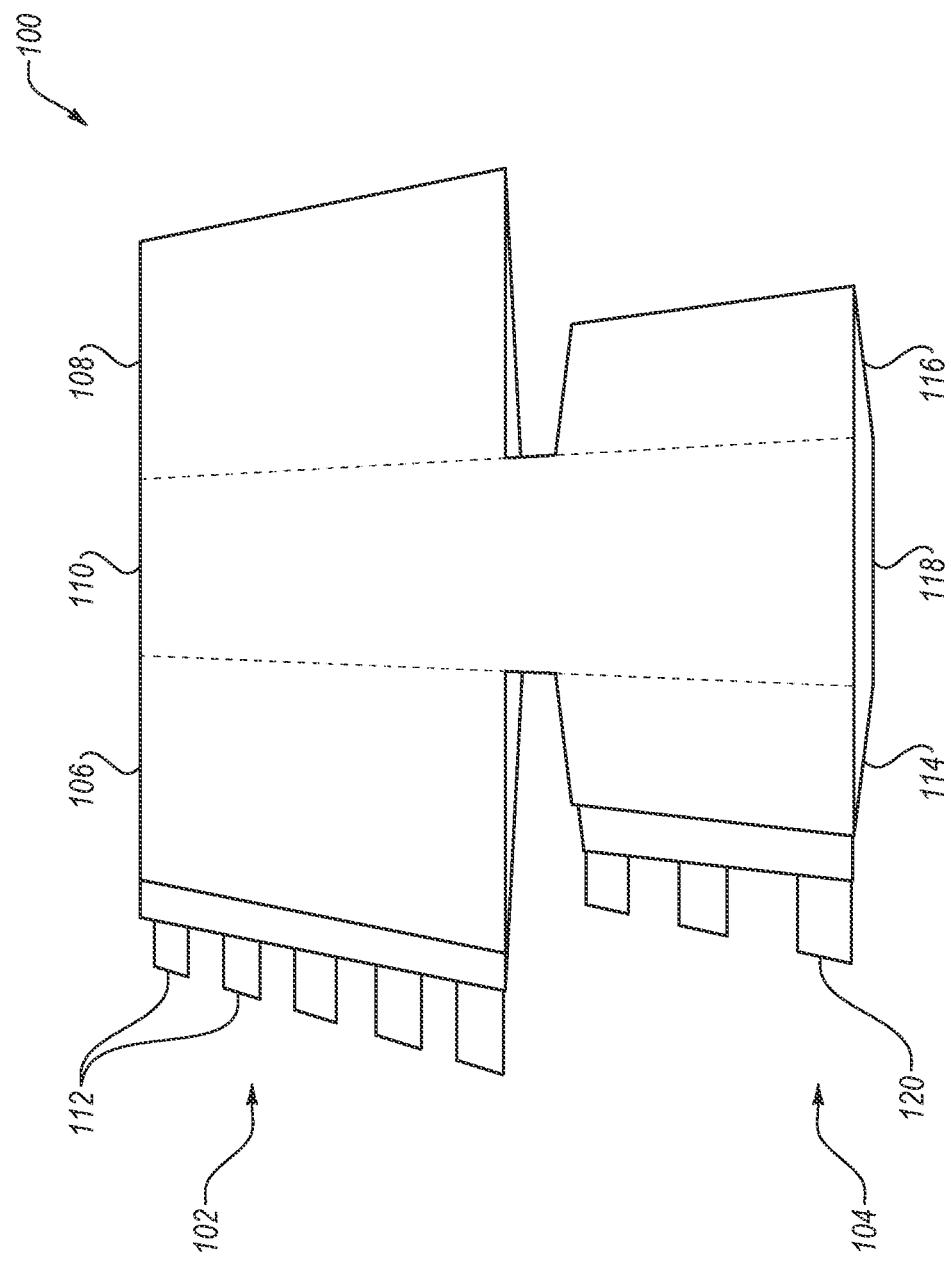

Turning to the figures, FIGS. 1A, 1B, and 1C illustrate a first exemplary absorbent wrap 100. FIGS. 1A and 1C illustrate a bottom or inside view of the absorbent wrap 100, while FIG. 1B illustrates a top or outside view of the absorbent wrap 100. FIG. 1C is a perspective view of the absorbent wrap 100. FIGS. 1A and 1C thus illustrate an inner surface 130 of the absorbent wrap 100 and FIG. 1B illustrates an outer surface 140 of the absorbent wrap 100.

The absorbent wrap 100 includes an upper portion 102 and a lower portion 104. The upper portion 102 includes a first upper wing 106, a second upper wing 108, a first center strip 110, and a first attachment mechanism 112. FIGS. 1A and 1C illustrate inner surfaces of each of these components while FIG. 1B illustrates outer surfaces of each of these components. One end of the first upper wing 106 is secured to the first center strip 110. One end of the second upper wing 108 is also secured to an opposite side of the first center strip 110. An opposite side of the first upper wing 106 includes the first attachment mechanism 112.

The lower portion 104 includes a first lower wing 114, a second lower wing 116, a second center strip 118, and a second attachment mechanism 120. FIGS. 1A and 1C illustrate inner surfaces of each of these components while FIG. 1B illustrates outer surfaces of each of these components. One end of the first lower wing 114 is secured to the second center strip 118. One end of the second lower 116 wing is also secured to an opposite side of the second center strip 118. An opposite side of the first lower wing 114 includes the second attachment mechanism 120.

There is a gap between the upper wings 106 and 108 and the lower wings 114 and 116, respectively, such that the upper wings 106 and 108 lack a direct connection with the lower wings 114 and 116. Rather, the first and second center strips 110 and 118 are connected to link the upper portion 102 with the lower portion 104 of the absorbent wrap 100. Thus, the upper wings 106 and 108 are indirectly connected with the lower wings 114 and 116 through the connection between center strips 110 and 118. The size and shape of the gap separating the upper wings 106 and 108 from the lower wings 114 and 116 can vary. In some embodiments, the gap may be small and in other embodiments the upper wings 106 and 108 may be separated from the lower wings 114 and 116 by a large gap. In some embodiments, the wings may have tapered shapes such that they become more narrow as they move away from the center strips. In these embodiments, the gaps between wings will increase toward the ends of the wings.

The absorbent wrap 100 is configured to be secured to an appendage of the human body. More specifically, the absorbent wrap 100 is configured to be secured to opposite sides of a joint, such as an ankle, knee, wrist, elbow, etc. The upper portion 102 is configured to be secured to one side of the joint and the lower portion 104 is configured to be secured to an opposite side of the joint. For example, in some embodiments, the upper portion 102 of the absorbent wrap 100 may be configured to be secured to a leg above the ankle and the lower portion 104 of the absorbent wrap 100 may be configured to be secured to a foot. The wings 106 and 108 of the upper portion 102 may be sized and shaped to slightly overlap when wrapped around a target appendage. Similarly, the wings 114 and 116 of the lower portion 104 may be sized and shaped to slightly overlap when wrapped around a target appendage. The sizes and shapes of the upper and lower portions 102 and 104 may vary depending on the intended use of the absorbent wrap 100. For example, in some embodiments, upper and lower portions may be symmetrical while in other embodiments, an upper portion may be larger or smaller or have a different shape than a lower portion.

In some embodiments, the upper portion 102 and the lower portion 104 may include a layered construction that comprises an absorbent material that is sandwiched between a fluid impermeable outer layer and a fluid permeable inner layer. The absorbent material may include a polymer or a polymer infused material, alginate, cotton, sponge, foam, or any other current or future absorbent technology. The fluid impermeable outer layer and the fluid permeable inner layer may be made from non-woven materials. In some embodiments, the fluid impermeable outer layer may be breathable such that gas may pass through the outer layer while liquids are retained.

In some embodiments, the inner surface 130 of the absorbent wrap 100, which includes the inner layers of the upper portion 102 and the lower portion 104, may be made from a unitary piece of non-woven material such that there are no seams in the inner surface 130 between, for example, the wings 106, 108, 114, 116 and the center strips 110, 118. Similarly, the outer surface 140 of the absorbent wrap 100, which includes the outer layers of the upper portion 102 and the lower portion 104, may be made from a unitary piece of non-woven material such that there are no seams in the outer surface 140 between, for example, the wings 106, 108, 114, 116 and the center strips 110, 118.

The first and second attachment mechanisms 112 and 120 may be self-attaching. As used herein, the term "self-attaching" means that the attachment mechanism is connected to the absorbent wrap and is also configured to be secured to the absorbent wrap. In other words, no external devices (such as clips, bands, sleeves, etc.), are required to secure the absorbent wrap to an appendage of the body. The attachment mechanism, if self-attaching, does not use a part of the body, such as the skin, as an anchor point. Rather, a self-attaching attachment mechanism is secured to an appendage by an attachment to itself.

With regard to the absorbent wrap 100, the first and second attachment mechanisms 112 and 120 comprise a plurality of adhesive strips that are secured to the first upper wing 106 and the first lower wing 114, respectively. These adhesive strips 112 and 120 may be secured to the outer surface 140 of the second upper wing 108 and the second lower wing 116, respectively. Thus, in order to secure the absorbent wrap 100 to the body, the first and second upper wings 106 and 108 are wrapped around an appendage on one side of a joint and secured to the appendage by the first attachment mechanism 112. The first and second lower wings 114 and 116 are then wrapped around an appendage on an opposite side of the joint and secured to the appendage by the second attachment mechanism 120.

In some embodiments, a self-attaching attachment mechanism may comprise two or more elements that interact to provide the desired attachment. For example, a self-attaching attachment mechanism may include a hook and loop fastener, such as Velcro®, with a hook element secured to one wing and a loop element secured to an outer surface of an opposing wing. A self-attaching attachment mechanism may include one or more clips, zippers, snaps, or buttons with opposing male and female elements that interface with each other. A self-attaching attachment mechanism may include one or more adhesive strips on one wing that interface with a non-porous surface on an outer surface of an opposing wing. A self-attaching attachment mechanism may also include a self-securing circumferential stretch material.

The first and second attachment mechanisms may also be selectively adjustable. As used herein, the term "selectively adjustable" means that the attachment mechanism is capable of being released and resecured. Thus, if the absorbent wrap becomes too tight due to an increase in swelling, the attachment mechanism may be released and the absorbent wrap may be resecured at a more comfortable, looser position. On the other hand, if the absorbent wrap becomes too loose due to a release of fluids, the attachment mechanism may be released and the absorbent wrap may be resecured at a more comfortable, tighter position.

In some embodiments, the absorbent wrap 100 may include a moisture indicator that provides a visual indication of the amount of liquid contained within the absorbent layer. This visual indication may be provided in any number of different ways. For example, in some embodiments different colors may correspond to different amounts of liquid such that as more liquid is retained in the absorbent layer, the color will change. In other embodiments, one or more images may appear as the amount of liquid contained within the absorbent layer increases.

Modifications, additions, or omissions may be made to the absorbent wrap 100 without departing from the scope of the present disclosure. For example, in some embodiments, the absorbent wrap 100 may include only a single wing in the upper portion 102 and/or a single wing in the lower portion 104.

Figure 2A:
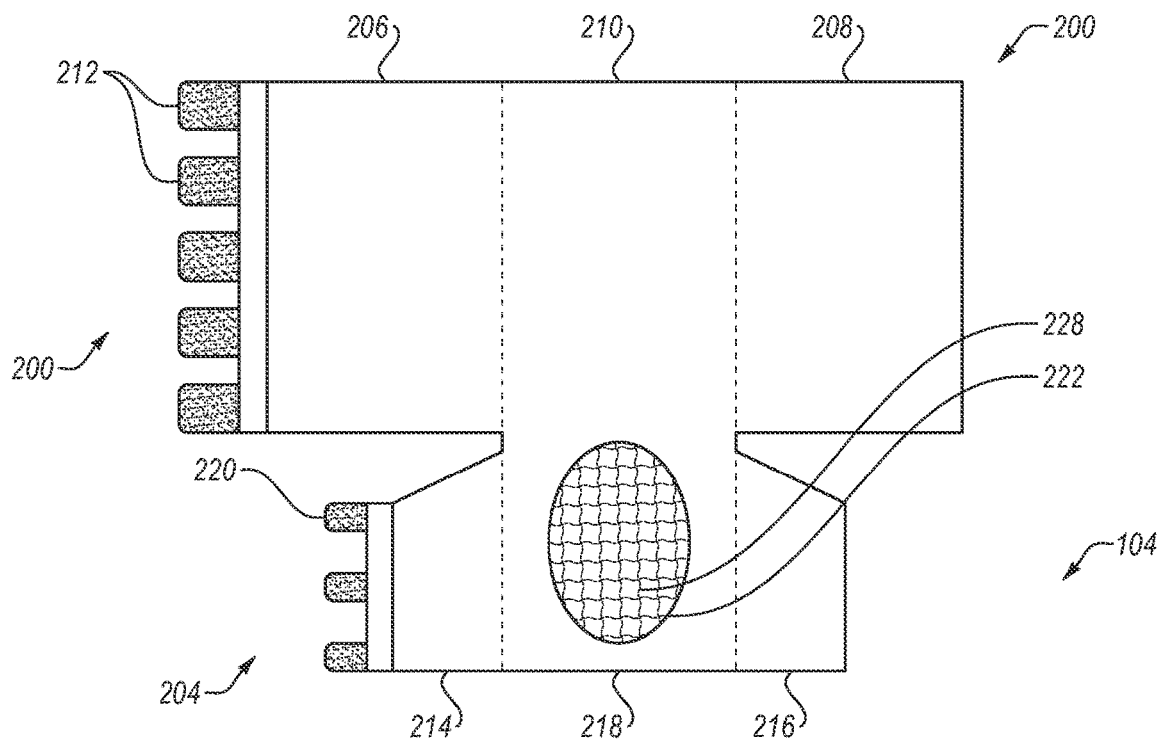
FIGS. 2A-2F illustrate a second exemplary absorbent wrap.
Figure 2B:
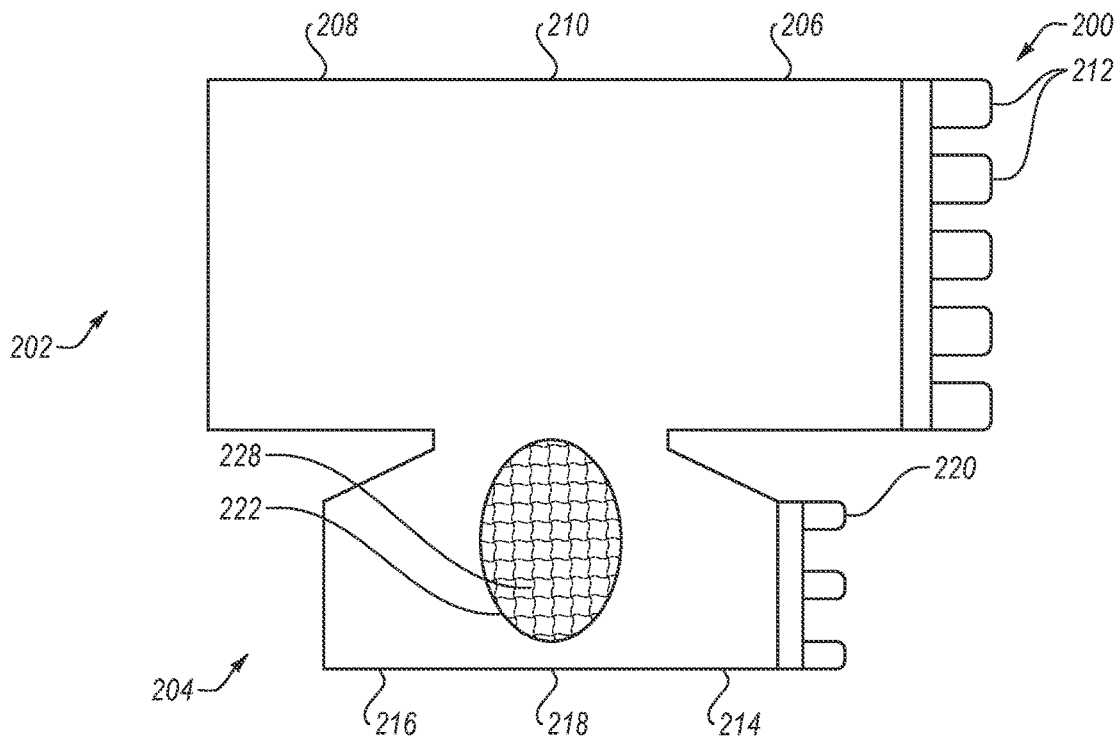

FIGS. 2A-2F illustrate a second exemplary absorbent wrap 200. The absorbent wrap 200 is a lower leg and foot wrap. FIG. 2A illustrates a bottom or inside view of the absorbent wrap 200, while FIG. 2B illustrates a top or outside view of the absorbent wrap 200. FIG. 2A thus illustrates an inner surface of the absorbent wrap 200 and FIG. 2B illustrates an outer surface of the absorbent wrap 200.

The absorbent wrap 200 includes a leg portion 202 and a foot portion 204. The leg portion 202 includes a first leg wing 206, a second leg wing 208, a first center strip 210, and a first attachment mechanism 212. The foot portion 204 includes a first foot wing 214, a second foot wing 216, a second center strip 218, a second attachment mechanism 220, and a heel segment 222. The heel segment 222 includes an elastic or other material 228. FIGS. 2A and 2B illustrate perspective views of the absorbent wrap 200.

There is a gap between the leg wings 206 and 208 and the foot wings 214 and 216, respectively, such that the leg wings 206 and 208 lack a direct connection with the foot wings 214 and 216. Rather, the first and second center strips 210 and 218 are connected to link the leg portion 202 with the foot portion 204 of the absorbent wrap 200. Thus, the leg wings 206 and 208 are indirectly connected with the foot wings 214 and 216 through the center strips 210 and 218.

Figure 2C:
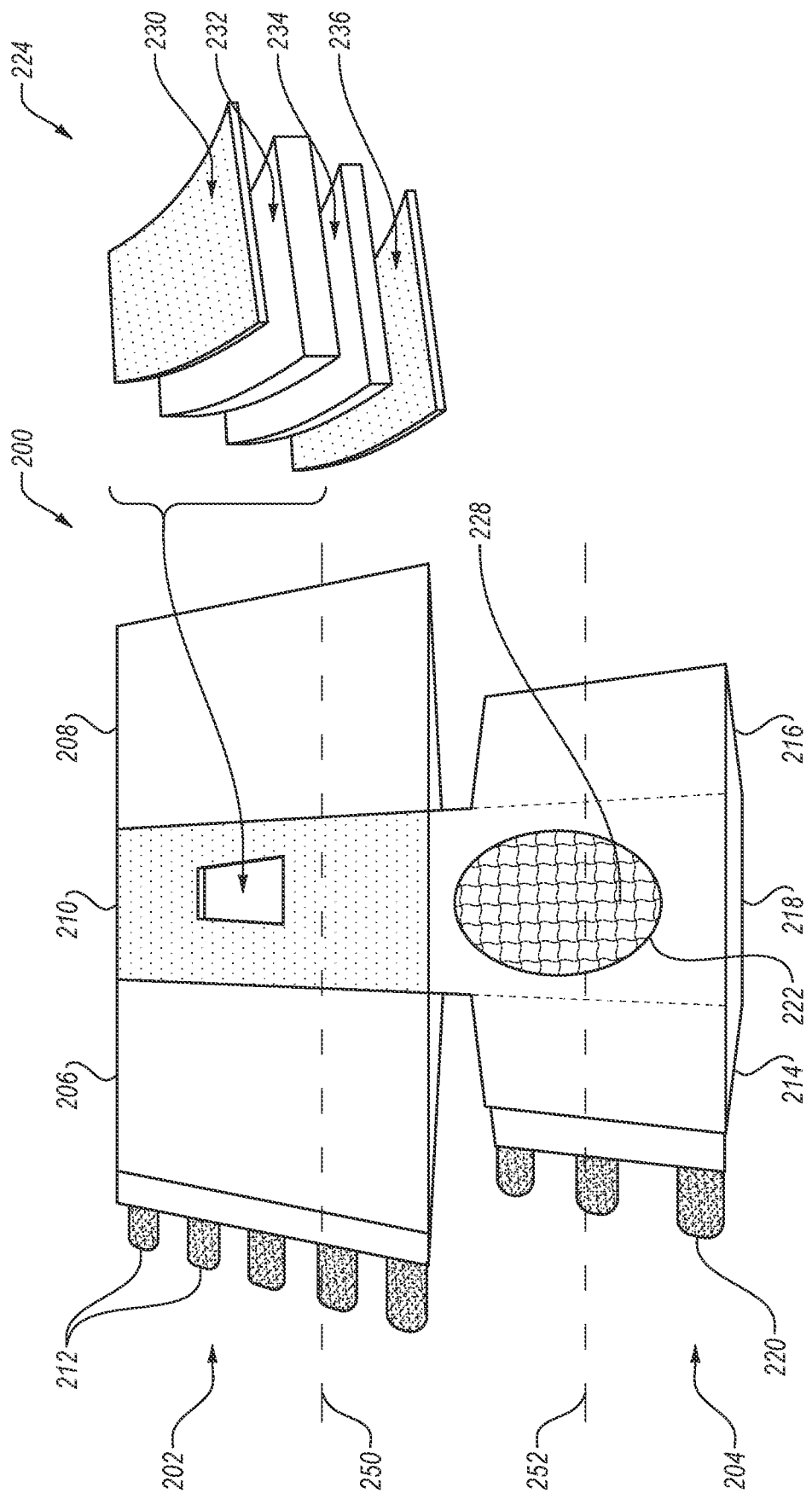

FIG. 2C is a perspective view of the absorbent wrap 200 and illustrates an exploded cut-away 224 from the first center strip 210, which shows the layered construction of the first center strip 210. This layered construction includes a fluid permeable inner layer 230, a first layer of absorbent material 234, a second layer of absorbent material 232, and a fluid impermeable outer layer 236. The first and second layers of absorbent material 234 and 232 may include a polymer. The fluid permeable inner layer 230 and the fluid impermeable outer layer 236 may be made from non-woven materials. In some embodiments, the fluid impermeable outer layer 236 may be breathable such that gas may pass through the outer layer while liquids are retained.

Figure 2D:
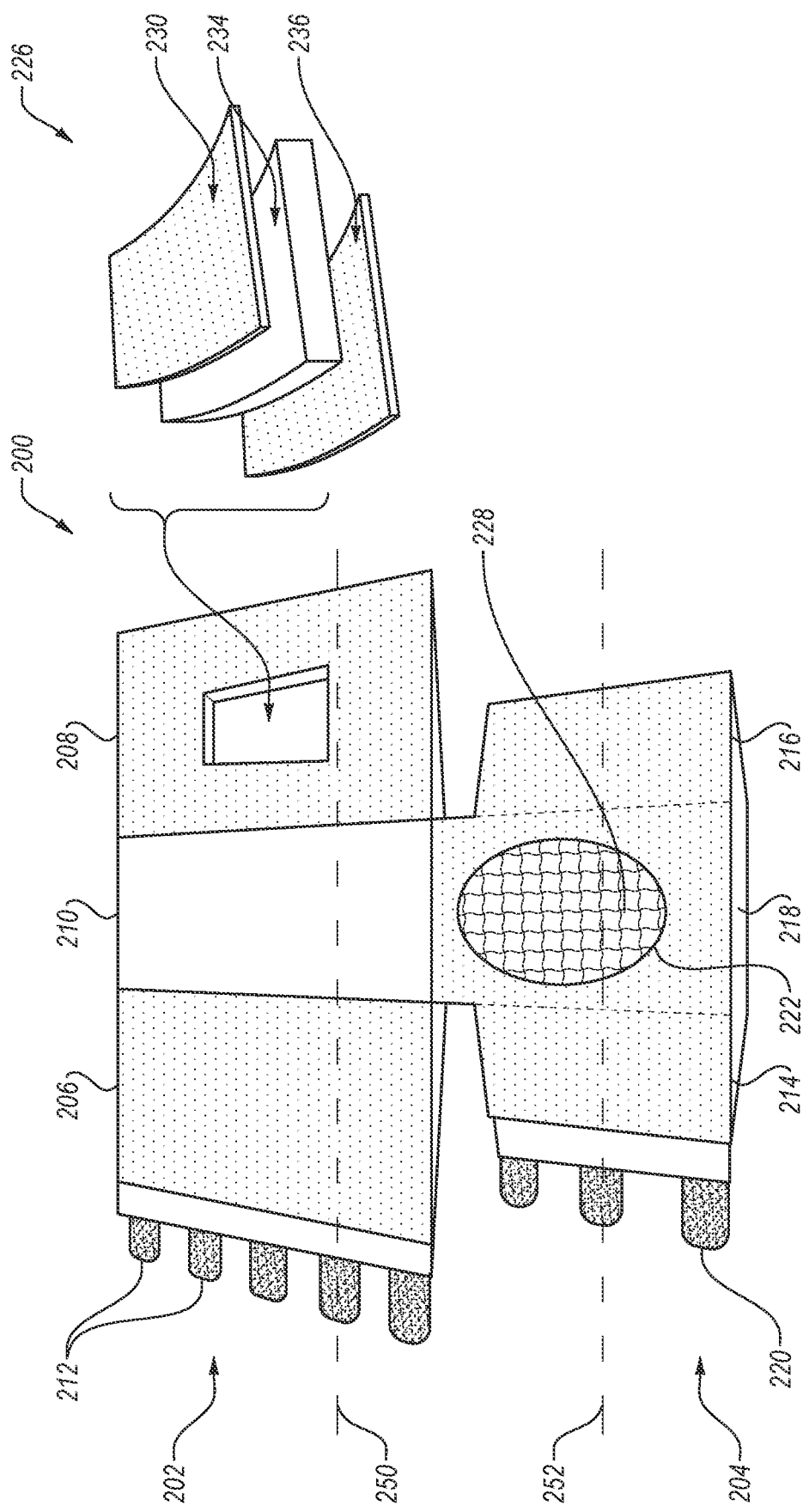

FIG. 2D is another perspective view of the absorbent wrap 200 and illustrates an exploded cut-away 226 from the second leg wing 208, which shows the layered construction of the second leg wing 208. This layered construction includes the fluid permeable inner layer 230, the first layer of absorbent material 234, and the fluid impermeable outer layer 236. Thus, the second leg wing 208 lacks the second layer of absorbent material 232 that is included in the first center strip 210.

The heel segment 222 may be sized, shaped, and positioned in the second center strip 218 to accommodate a user's heel. The heel segment 222 may lack the layered construction shown in cut-aways 224 and 226. In the absorbent wrap 200, the heel segment 222 includes an elastic or other material 228. In other embodiments, the heel segment 222 may be an aperture that lacks any layers. A heel segment may have any size and shape. The heel segment 222, for example, has an oval shape.

Figure 2E:
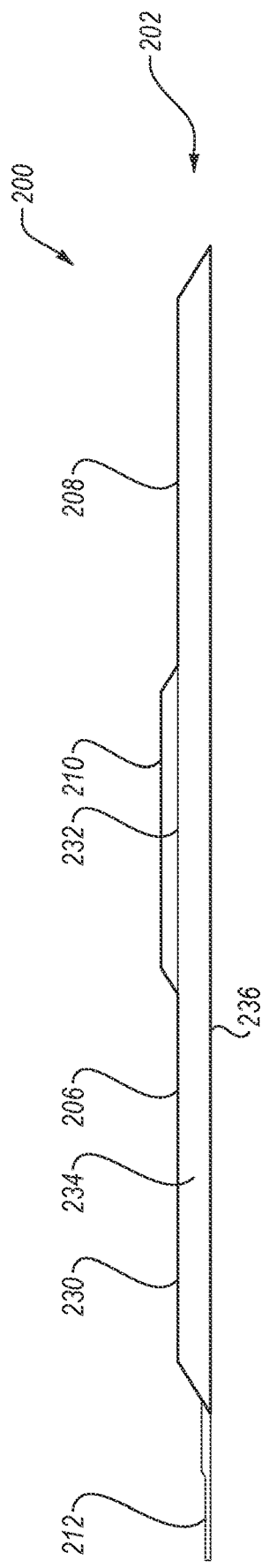

In some embodiments, the single absorbent layer construction shown in the second leg wing 208 may be shared by the first leg wing 206, the first and second foot wings 214 and 216, and the second center strip 218. The double layer of absorbent material may be limited to the first center strip 210. For example, FIG. 2E illustrates a cross-sectional view of the leg portion 202 cut along a plane 250. As can be seen in FIG. 2E, the first layer of absorbent material 234 extends across the entire leg portion 202. It is only the first center strip 210 that includes the second layer of absorbent material 232.

Figure 2F:
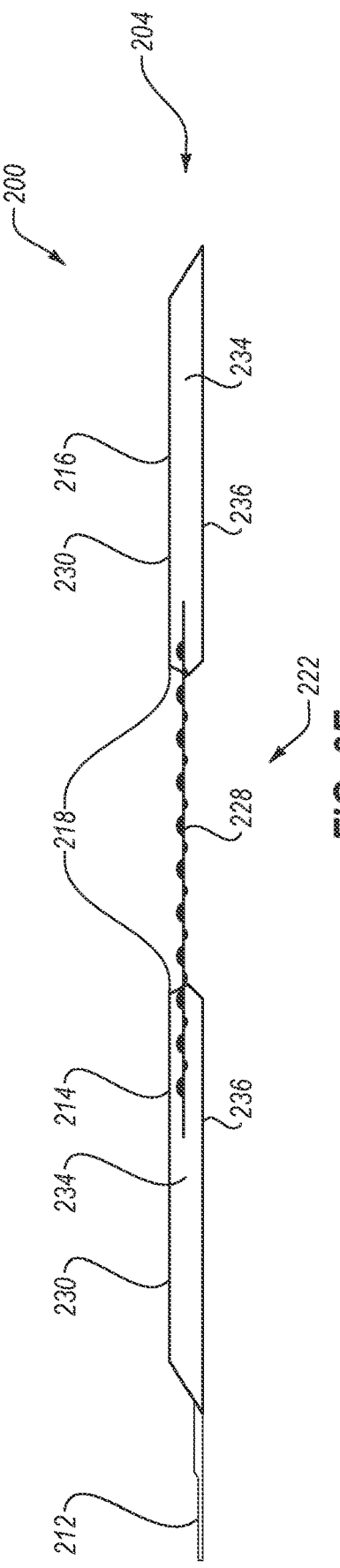

FIG. 2F illustrates a cross-sectional view of the foot portion 204 cut along a plane 252. As can be seen in FIG. 2F, the first layer of absorbent material 234 is not included in the heel segment 222. Rather, the heel segment 222 includes a material 228 that provides additional comfort for a heel. This material may be, for example, an elastic material.

Modifications, additions, or omissions may be made to the absorbent wrap 200 without departing from the scope of the present disclosure. For example, in some embodiments, additional portions of an absorbent wrap may include a second layer of absorbent material. For example, in some embodiments, all of a leg portion of an absorbent wrap may include a two (or more) layers of absorbent material. In other embodiments, all of the absorbent wrap may include two (or more) layers of absorbent material.

Figure 3A:
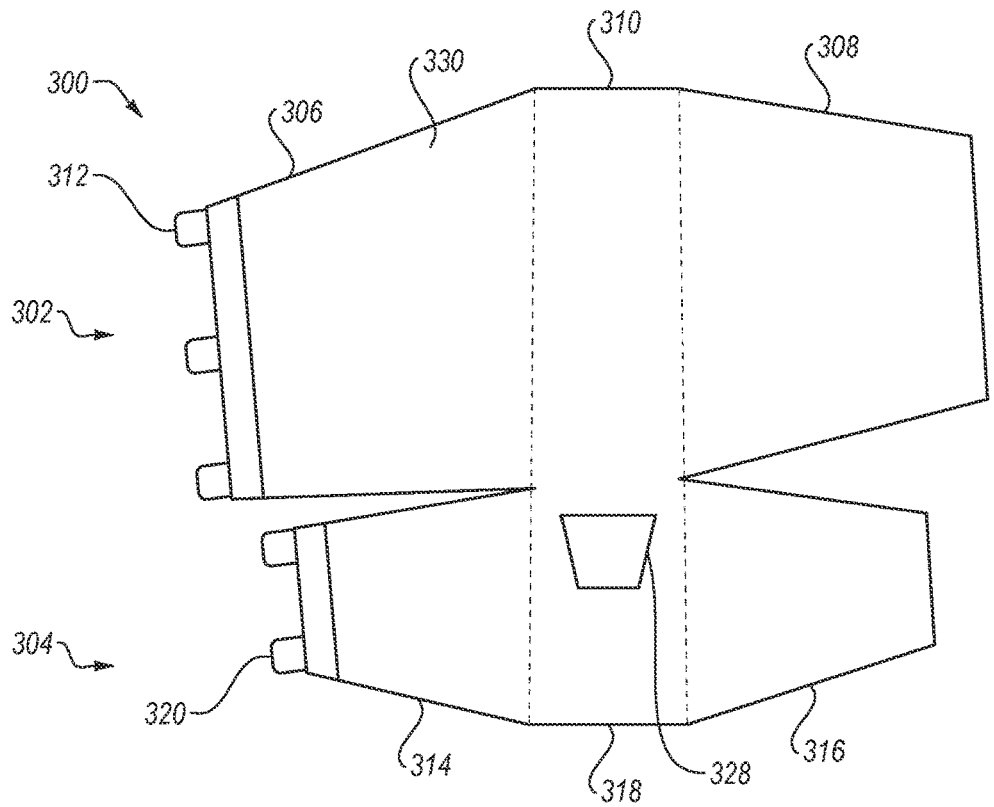
FIGS. 3A-3C illustrate a third exemplary absorbent wrap.
Figure 3B:
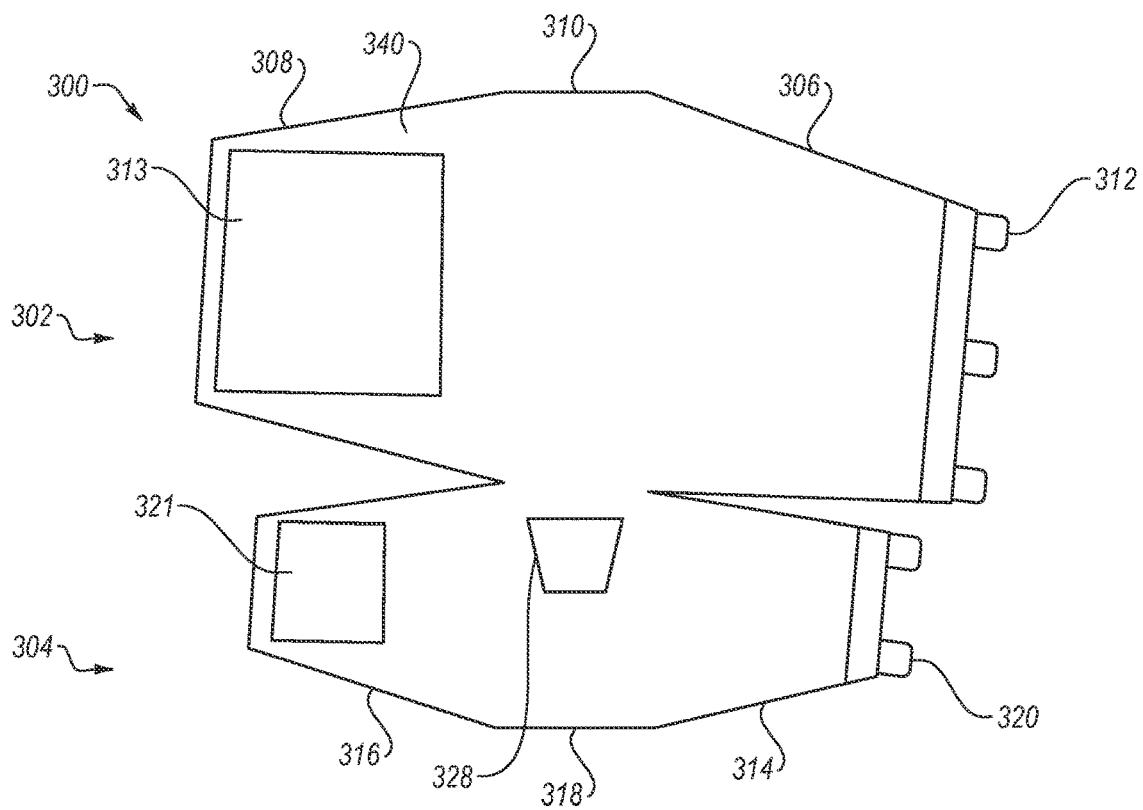
Figure 3C:
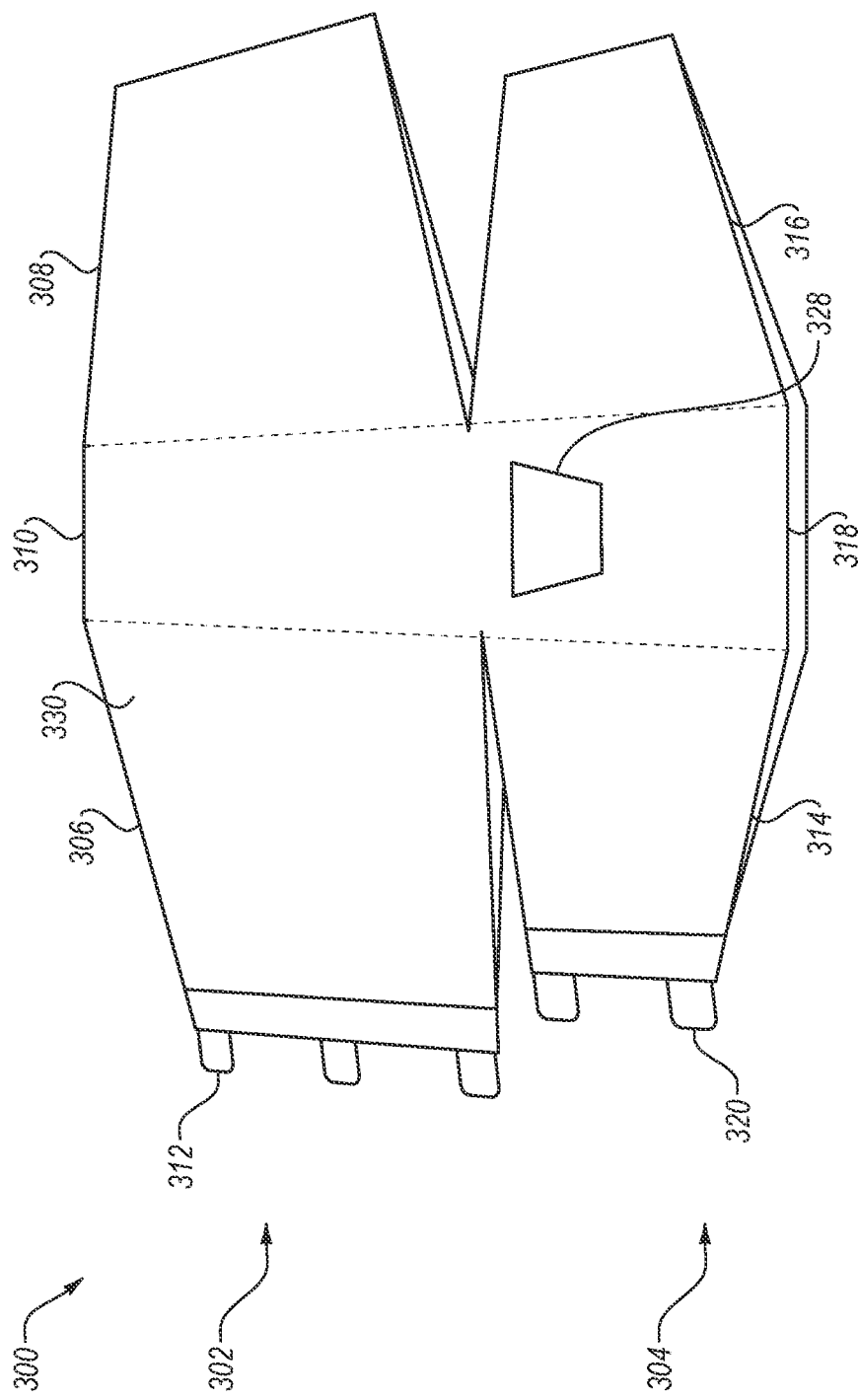

FIGS. 3A, 3B, and 3C illustrate a third exemplary absorbent wrap 300. FIGS. 3A and 3C illustrate a bottom or inside view of the absorbent wrap 300, while FIG. 3B illustrates a top or outside view of the absorbent wrap 300. FIG. 3C is a perspective view of the absorbent wrap 300. FIGS. 3A and 3C thus illustrate an inner surface 330 of the absorbent wrap 300 and FIG. 3B illustrates an outer surface 340 of the absorbent wrap 300.

The absorbent wrap 300 includes an upper portion 302 and a lower portion 304. The upper portion 302 includes a first upper wing 306, a second upper wing 308, a first center strip 310, a first attachment mechanism 312, and a second attachment mechanism 313. One end of the first upper wing 306 is secured to the first center strip 310. One end of the second upper wing 308 is also secured to an opposite side of the first center strip 310. An opposite side of the first upper wing 306 includes the first attachment mechanism 312. An outer surface of the second upper wing 308 includes the second attachment mechanism 313.

The lower portion 304 includes a first lower wing 314, a second lower wing 316, a second center strip 318, a third attachment mechanism 320, and a fourth attachment mechanism 321. One end of the first lower wing 314 is secured to the second center strip 318. One end of the second lower 316 wing is also secured to an opposite side of the second center strip 318. An opposite side of the first lower wing 314 includes the third attachment mechanism 320. An outer surface of the second lower wing 316 includes the fourth attachment mechanism 321. The second center strip 318 also includes a heel segment 328.

The absorbent wrap 300 may include the same layered construction described in connection with the absorbent wrap 200, above. Specifically, the first upper wing 306, the second upper wing 308, the first center strip 310, the first lower wing 314, the second lower wing 316, and the second center strip 318 may include a fluid permeable inner layer, one or more layers of absorbent material, and a fluid impermeable outer layer.

The first attachment mechanism 312 and the second attachment mechanism 313 may interface to create a secure, but selectively adjustable, attachment. Similarly, the third attachment mechanism 320 and the fourth attachment mechanism 321 may interface to create a secure, but selectively adjustable, attachment. For example, the first and second attachment mechanisms 312 and 313 may be hook and loop patches. For example, the first attachment mechanism 312 and/or third attachment mechanism 320 may include hook patches while the second attachment mechanism 313 and/or fourth attachment mechanism 321 may include a loop patch. Alternatively, the first attachment mechanism 312 and/or third attachment mechanism 320 may include adhesive tape while the second attachment mechanism 313 and/or fourth attachment mechanism 321 may include a non-porous surface to which the adhesive tape sticks.

Upper wings and lower wings may, but need not be, symmetrical. For example, in the absorbent wrap 300 the first upper wing 306 and the second upper wing 308 are asymmetrical. Similarly, the first lower wing 314 and the second lower wing 316 are asymmetrical. The asymmetrical design may allow for a smooth, wrinkle-free wrapping around an extremity, such as a leg and/or foot, to maximize contact of absorbent material to the skin. In addition, a heel segment may have any shape or size. In the absorbent wrap 300, the heel segment 328 has a trapezoidal shape. Modifications, additions, or omissions may be made to the absorbent wrap 300 without departing from the scope of the present disclosure.

Figure 4A:
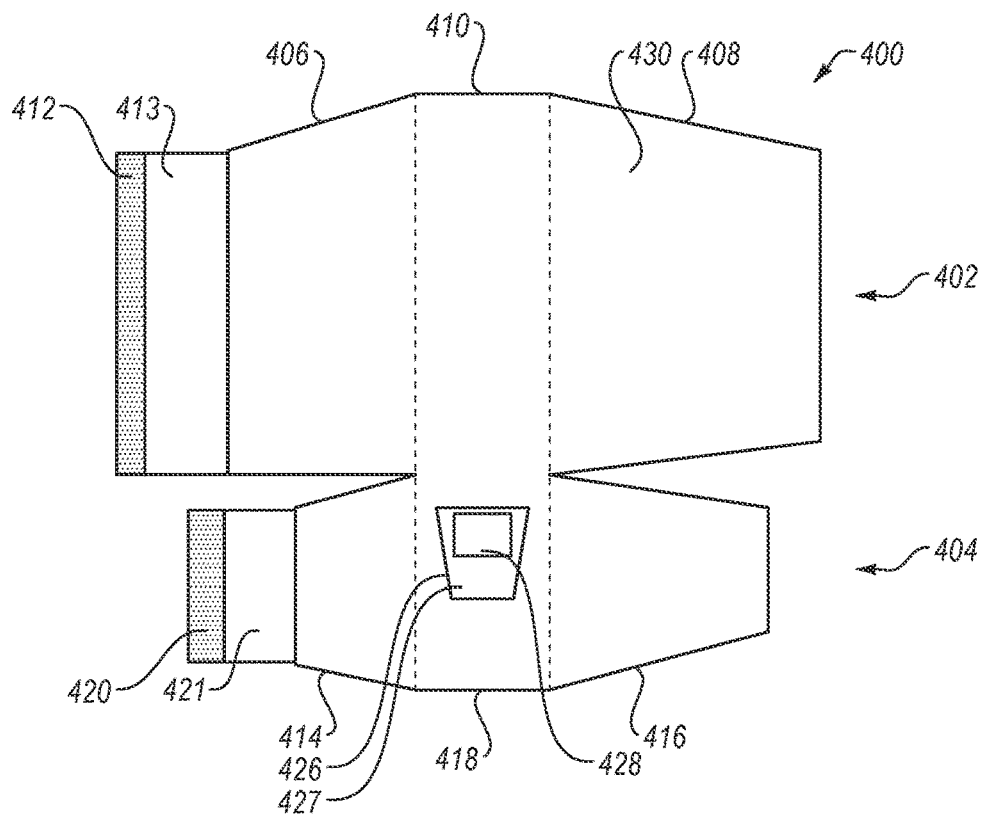
FIGS. 4A-4C illustrate a fourth exemplary absorbent wrap.
Figure 4B:
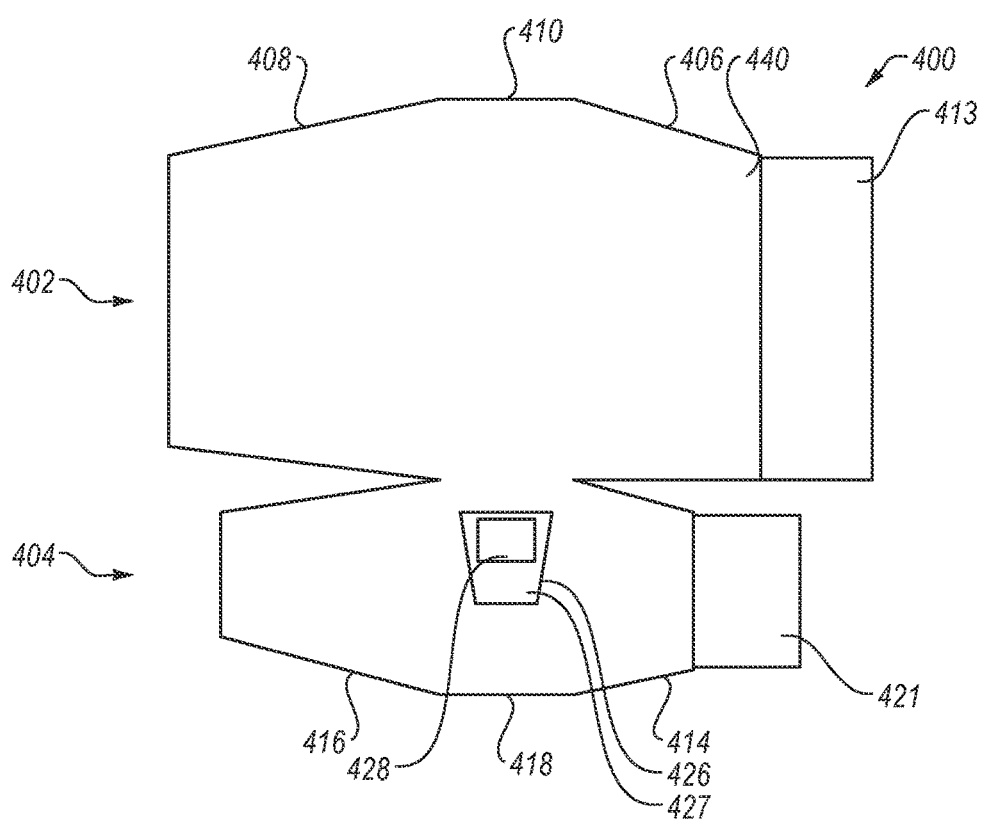
Figure 4C:
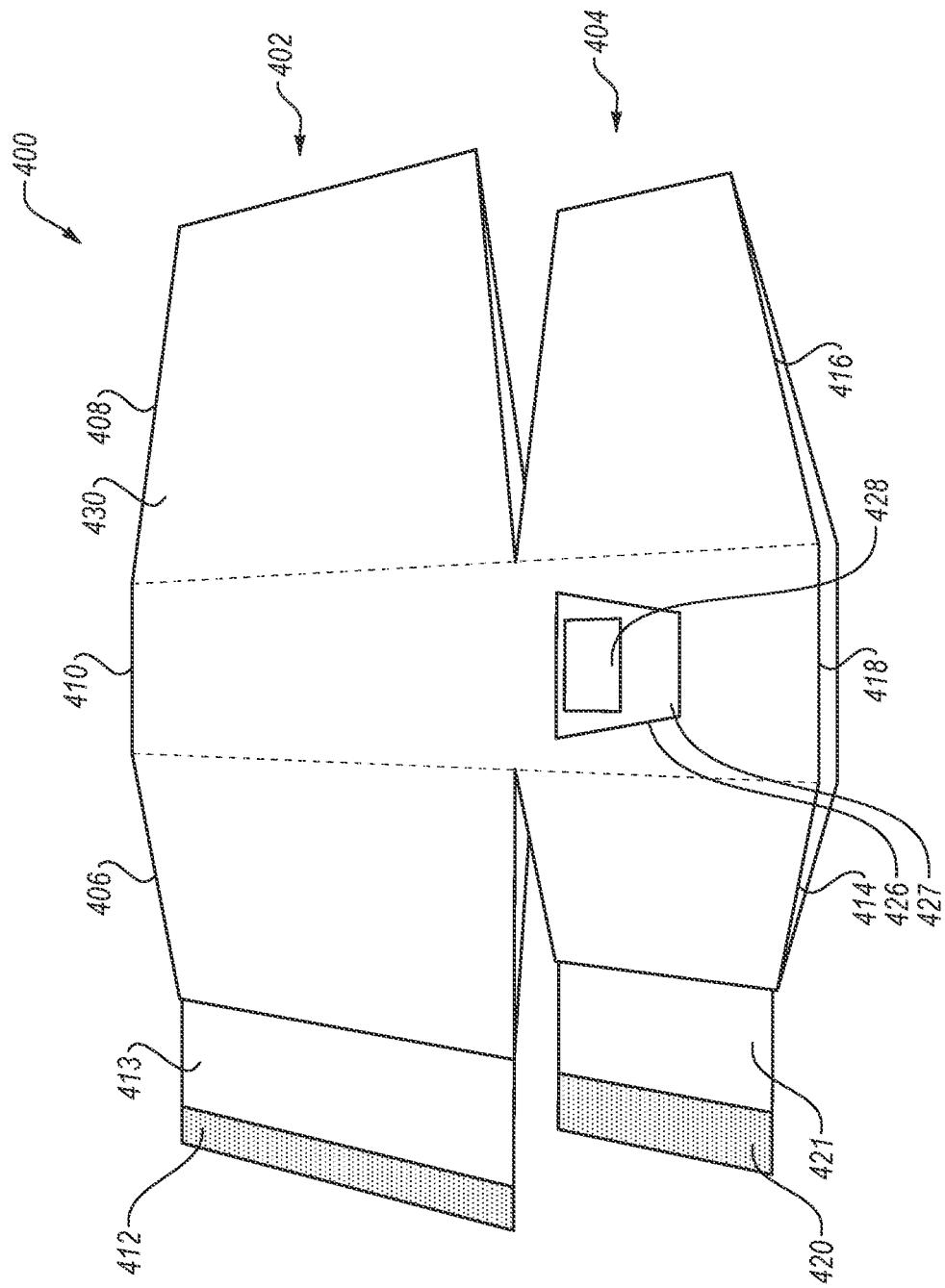

FIGS. 4A, 4B, and 4C illustrate a fourth exemplary absorbent wrap 400. FIGS. 4A and 4C illustrate a bottom or inside view of the absorbent wrap 400, while FIG. 4B illustrates a top or outside view of the absorbent wrap 400. FIG. 4C is a perspective view of the absorbent wrap 400. FIGS. 4A and 4C thus illustrate an inner surface 430 of the absorbent wrap 400 and FIG. 4B illustrates an outer surface 440 of the absorbent wrap 400.

The absorbent wrap 400 includes an upper portion 402 and a lower portion 404. The upper portion 402 includes a first upper wing 406, a second upper wing 408, a first center strip 410, and a first attachment mechanism 412. FIGS. 4A and C illustrate inner surfaces of each of these components while FIG. 4B illustrates outer surfaces of each of these components. One end of the first upper wing 406 is secured to the first center strip 410. One end of the second upper wing 408 is also secured to an opposite side of the first center strip 410. An opposite side of the first upper wing 406 includes the first attachment mechanism 412.

The lower portion 404 includes a first lower wing 414, a second lower wing 416, a second center strip 418, and a second attachment mechanism 420. FIGS. 4A and 4C illustrate inner surfaces of each of these components while FIG. 4B illustrates outer surfaces of each of these components. One end of the first lower wing 414 is secured to the second center strip 418. One end of the second lower wing 416 is also secured to an opposite side of the second center strip 418. An opposite side of the first lower wing 414 includes the second attachment mechanism 420. The second center strip 418 also includes a heel segment 426.

The absorbent wrap 400 may include the same layered construction described in connection with the absorbent wrap 200, above. Specifically, the first upper wing 406, the second upper wing 408, the first center strip 410, the first lower wing 414, the second lower wing 416, and the second center strip 418 may include a fluid permeable inner layer, one or more layers of absorbent material, and a fluid impermeable outer layer.

The first and second attachment mechanisms 412 and 420 may be self-attaching and selectively adjustable. For example, the first and second attachment mechanisms 412 and 420 may include strips of hook/loop material that are configured to interface with and stick to strips of hook/loop material on an outer surface of opposing upper and lower wings 408 and 416, respectively. The heel segment 426 in the second center strip 418 may include an elastic material portion 427 and an aperture 428 that lacks any elastic material but is simply an opening in the absorbent wrap 400.

The first attachment mechanism 412 may be secured to the first upper wing 406 through a connecting segment 413. Similarly, the second attachment mechanism 420 may be secured to the first lower wing 414 through a connecting segment 421. The connecting segments 413 and 421 may be any material. In some embodiments, the connecting segments 413 and 421 may include an elastic or stretchable material that allows for some expansion and contraction when secured to an appendage. Modifications, additions, or omissions may be made to the absorbent wrap 400 without departing from the scope of the present disclosure.

Figure 5A:
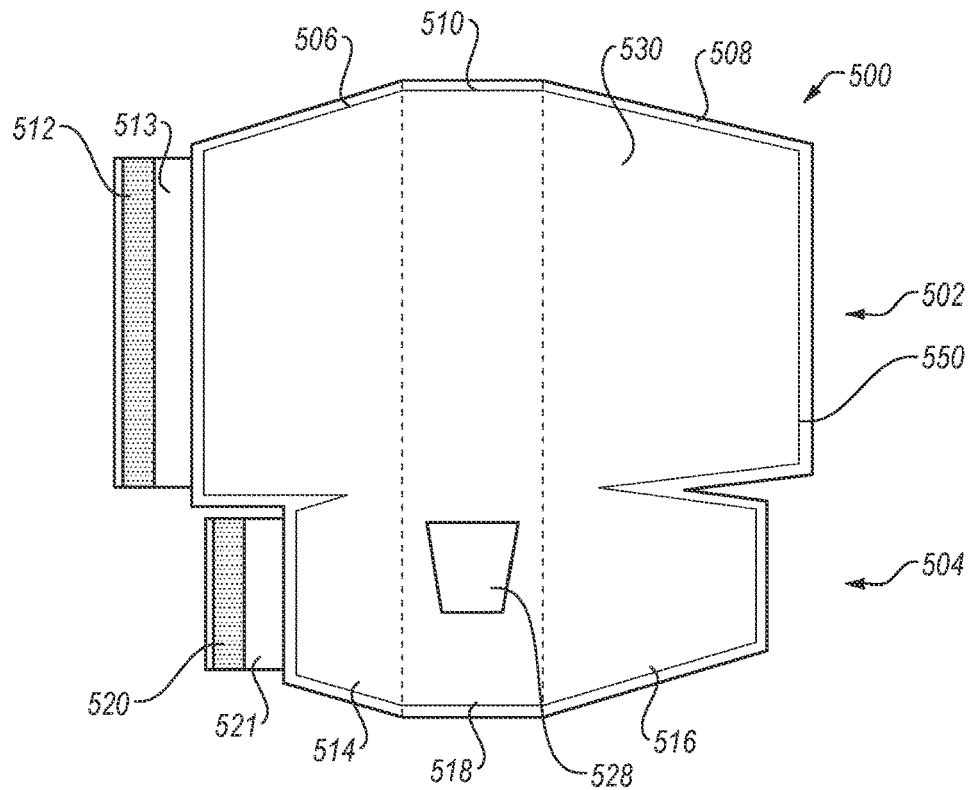
FIGS. 5A-5C illustrate a fifth exemplary absorbent wrap.
Figure 5B:
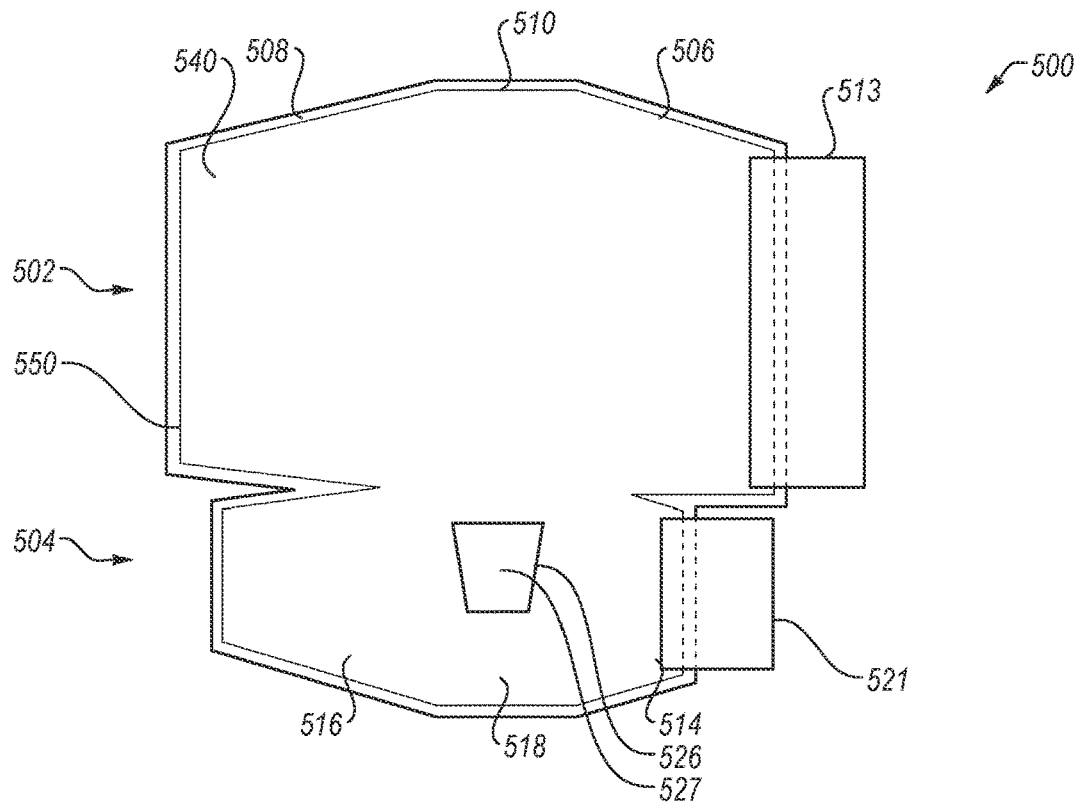
Figure 5C:
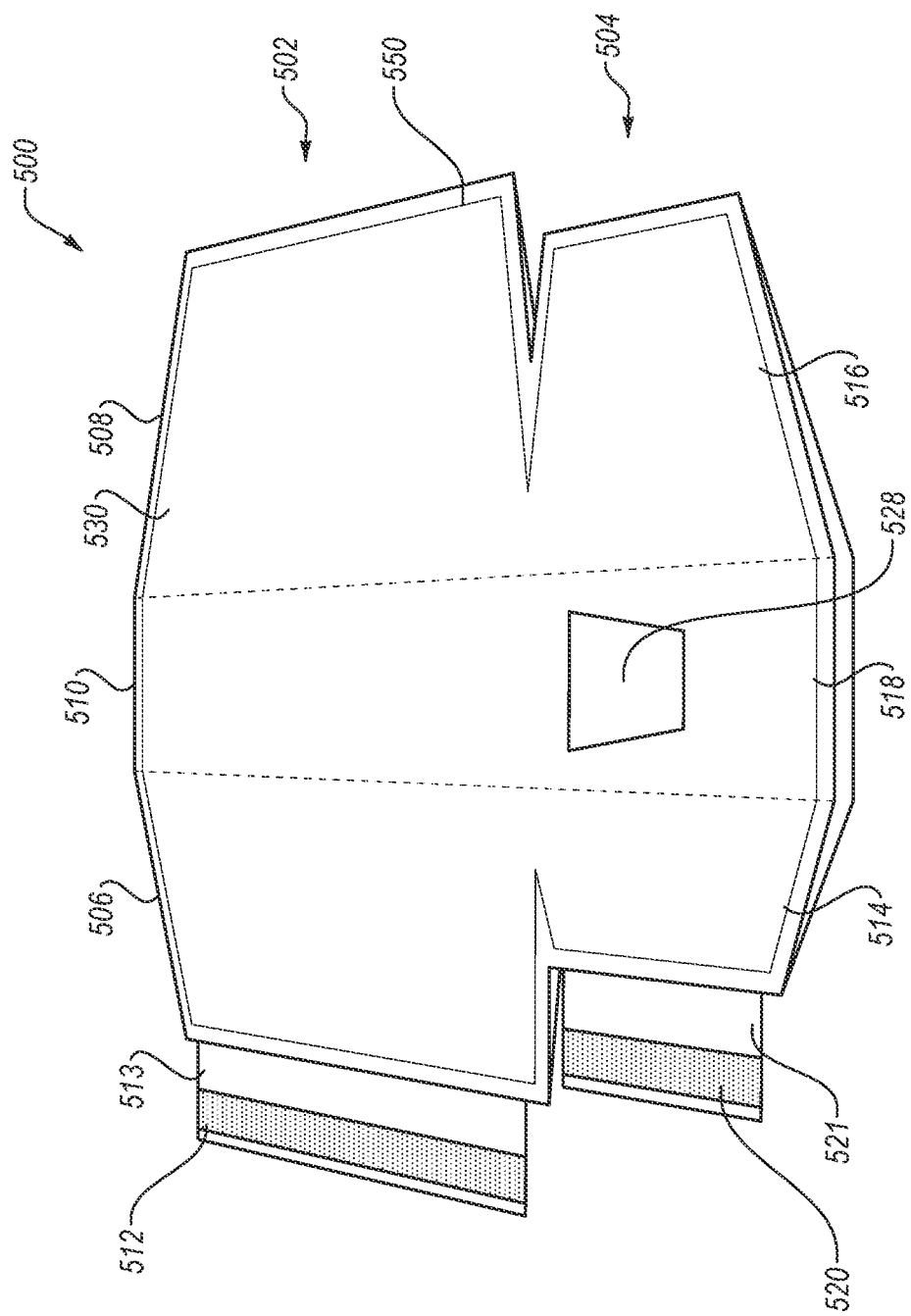

FIGS. 5A, 5B, and 5C illustrate a fifth exemplary absorbent wrap 500. FIGS. 5A and 5C illustrate a bottom or inside view of the absorbent wrap 500, while FIG. 5B illustrates a top or outside view of the absorbent wrap 500. FIG. 5C is a perspective view of the absorbent wrap 500. FIGS. 5A and 5C thus illustrate an inner surface 530 of the absorbent wrap 500 and FIG. 5B illustrates an outer surface 540 of the absorbent wrap 500.

The absorbent wrap 500 includes an upper portion 502 and a lower portion 504. The upper portion 502 includes a first upper wing 506, a second upper wing 508, a first center strip 510, and a first attachment mechanism 512. FIGS. 5A and 5C illustrate inner surfaces of each of these components while FIG. 5B illustrates outer surfaces of each of these components. One end of the first upper wing 506 is secured to the first center strip 510. One end of the second upper wing 508 is also secured to an opposite side of the first center strip 510. An opposite side of the first upper wing 506 includes the first attachment mechanism 512.

The lower portion 504 includes a first lower wing 514, a second lower wing 516, a second center strip 518, and a second attachment mechanism 520. FIGS. 5A and 5C illustrate inner surfaces of each of these components while FIG. 5B illustrates outer surfaces of each of these components. One end of the first lower wing 514 is secured to the second center strip 518. One end of the second lower wing 516 is also secured to an opposite side of the second center strip 518. An opposite side of the first lower wing 514 includes the second attachment mechanism 520. The second center strip 518 also includes a heel segment 526.

The absorbent wrap 500 also includes a bordered edge 550 that surrounds the perimeter of the wrap 500. This bordered edge 550 may be an additional seam or a bonding mechanism that adds structural integrity to the connection interfaces between the inner surface 530 and the outer surface 540.

The absorbent wrap 500 may include the same layered construction described in connection with the absorbent wrap 200, above. Specifically, the first upper wing 506, the second upper wing 508, the first center strip 510, the first lower wing 514, the second lower wing 516, and the second center strip 518 may include a fluid permeable inner layer, one or more layers of absorbent material, and a fluid impermeable outer layer.

The first and second attachment mechanisms 512 and 520 may be self-attaching and selectively adjustable. For example, the first and second attachment mechanisms 512 and 520 may include strips of hook/loop material that are configured to interface with and stick to strips of hook/loop material on an outer surface of opposing upper and lower wings 508 and 516, respectively. The heel segment 526 in the second center strip 518 may include an elastic material portion 527.

The first attachment mechanism 512 may be secured to the first upper wing 506 through a connecting segment 513. Similarly, the second attachment mechanism 520 may be secured to the first lower wing 514 through a connecting segment 521. The connecting segments 513 and 521 may be any material. In some embodiments, the connecting segments 513 and 521 may include an elastic or stretchable material that allow for some expansion and contraction when secured to an appendage. In addition, the absorbent wrap 500 may include an embossed or sealed outer edge. Modifications, additions, or omissions may be made to the absorbent wrap 500 without departing from the scope of the present disclosure.

Figure 6A:
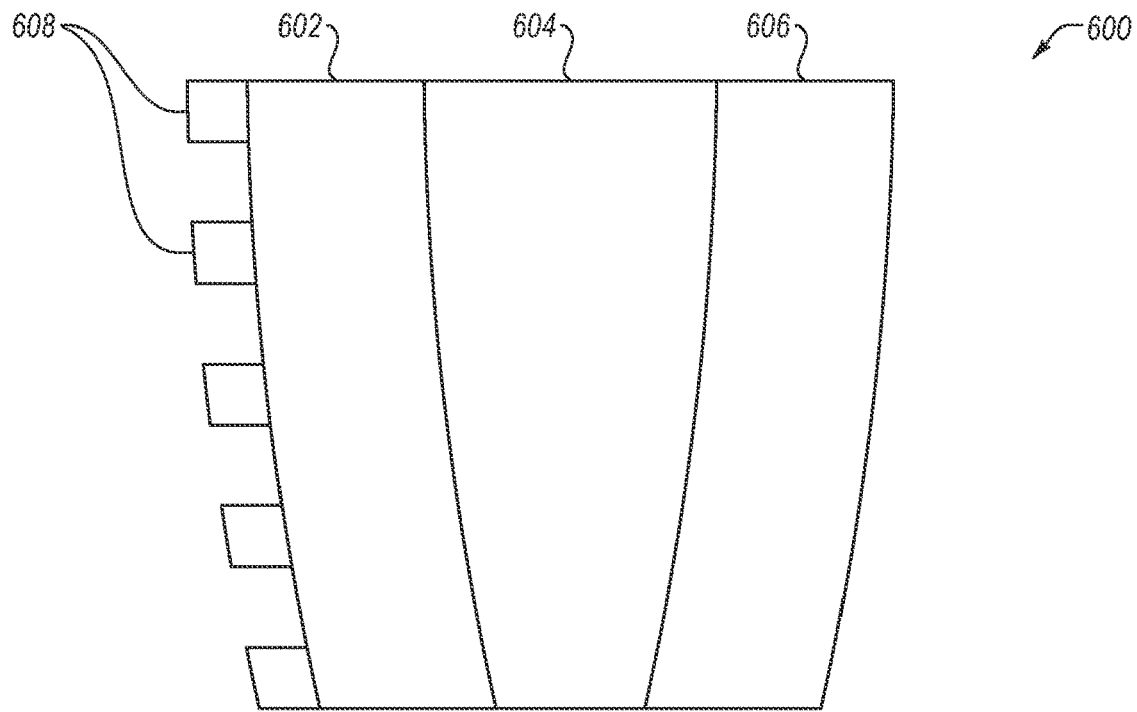
FIGS. 6A-6C illustrate a sixth exemplary absorbent wrap.
Figure 6B:
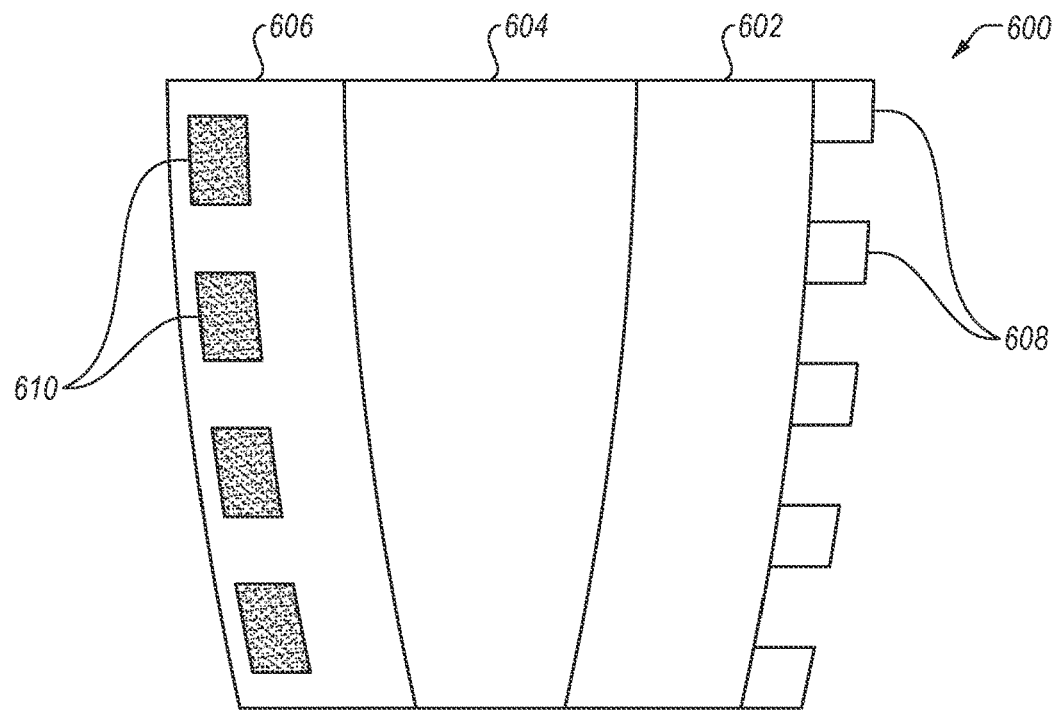
Figure 6C:
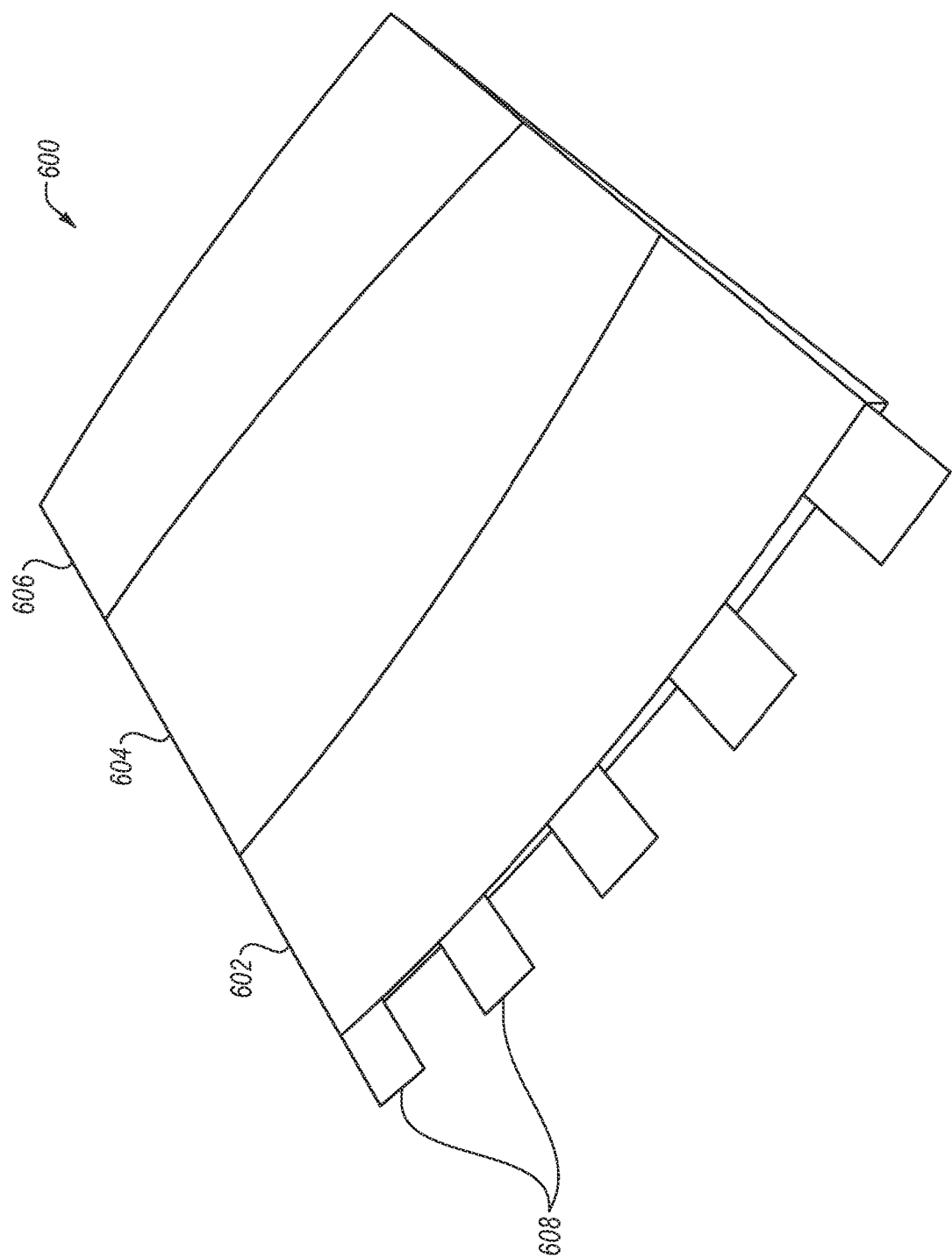

FIGS. 6A, 6B, ad 6C illustrate a sixth exemplary absorbent wrap 600. FIG. 6A illustrates a bottom or inside view of the absorbent wrap 600, while FIG. 6B illustrates a top or outside view of the absorbent wrap 600. FIG. 6C is a perspective view of the absorbent wrap 600. FIG. 6A thus illustrates an inner surface of the absorbent wrap 600 and FIG. 6B illustrates an outer surface of the absorbent wrap 600.

The absorbent wrap 600 includes a first wing 602, a center strip 604, a second wing 606, and a first attachment mechanism 608, and a second attachment mechanism 610. One end of the first wing 602 is secured to the center strip 604. One end of the second wing 606 is also secured to an opposite side of the center strip 604. An opposite side of the first wing 602 includes the first attachment mechanism 608. As can be seen in FIG. 6B, the outer surface of the second wing 606 includes the second attachment mechanism 610. The first and second attachment mechanisms 608 and 610 may be self-attaching and selectively adjustable. For example, the first and second attachment mechanisms 608 and 610 may include strips of hook and loop material that are configured to interface with and stick the first and second wings 602 and 606 together.

The absorbent wrap 600 may include the same layered construction described in connection with the absorbent wrap 200, above. Specifically, the first wing 602, the center strip 604, and the second wing 606 may include a fluid permeable inner layer, one or more layers of absorbent material, and a fluid impermeable outer layer. Modifications, additions, or omissions may be made to the absorbent wrap 600 without departing from the scope of the present disclosure.

Figure 7A:
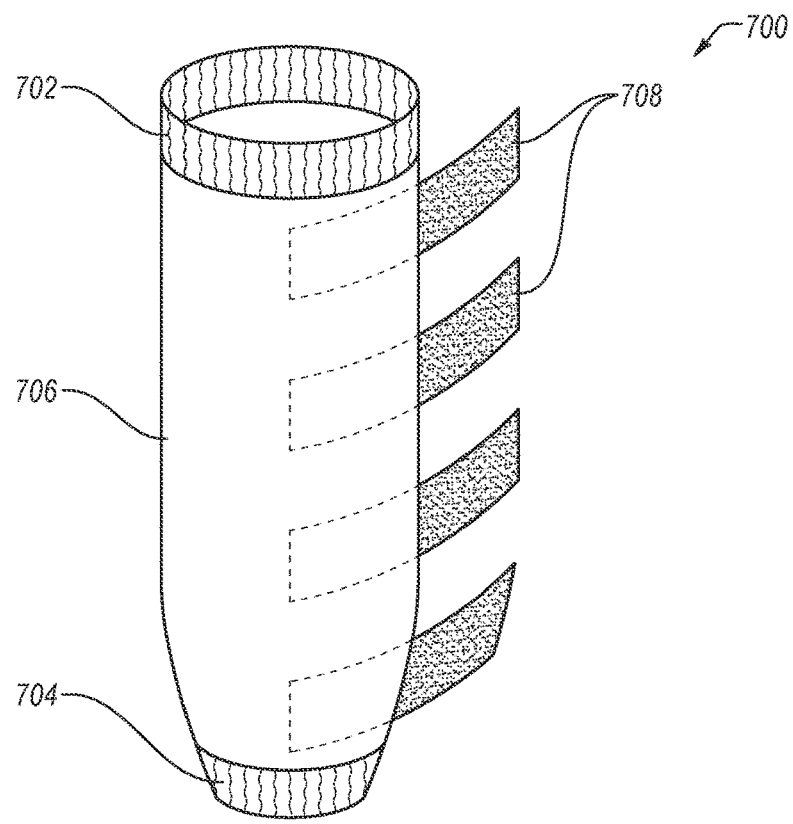
FIGS. 7A-7D illustrate a seventh exemplary absorbent wrap.
Figure 7B:
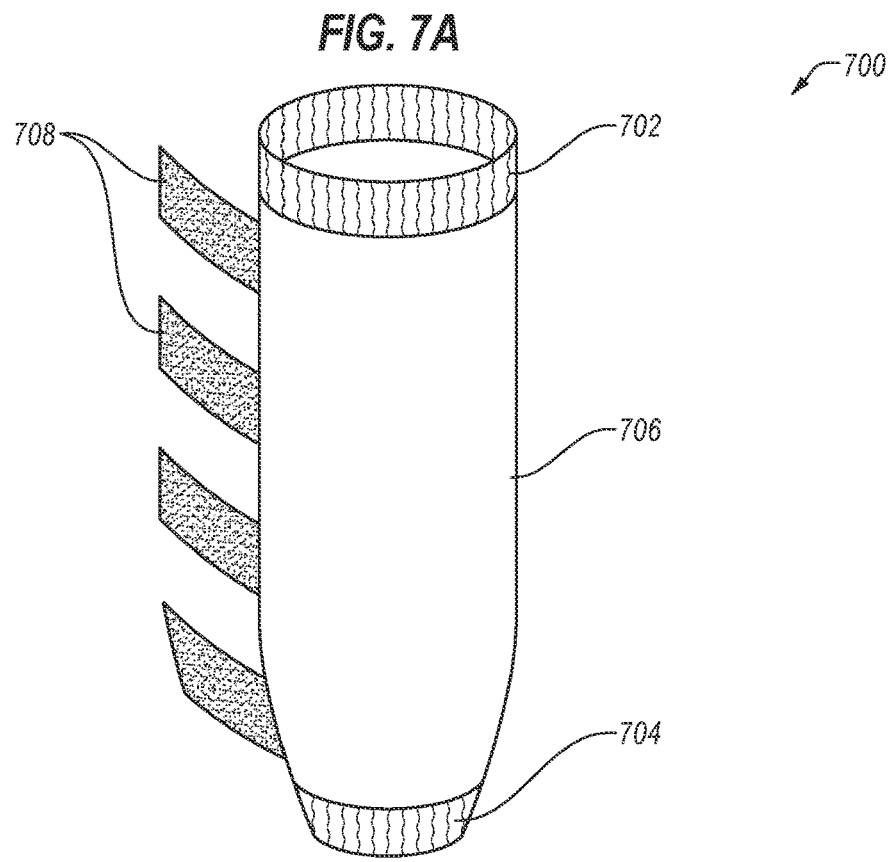
Figure 7C:
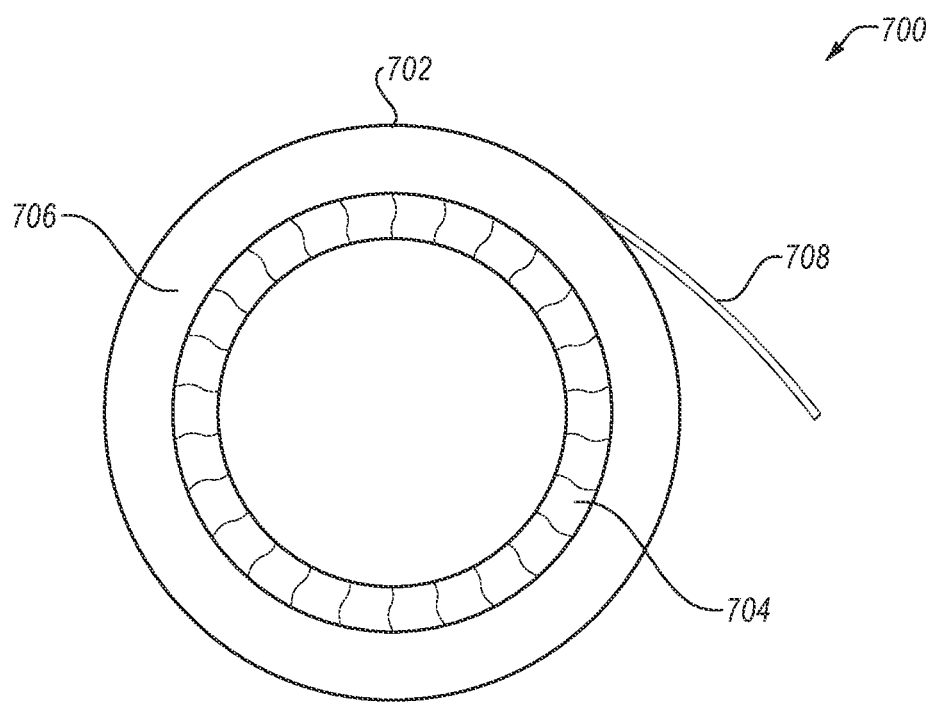
Figure 7D:
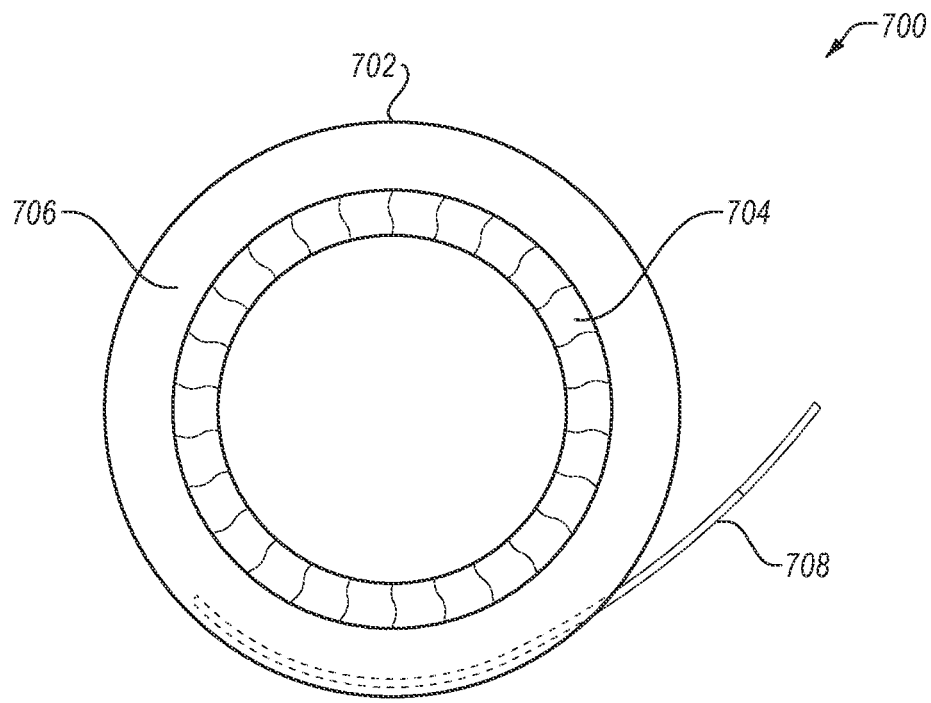

FIGS. 7A-7D illustrate a seventh exemplary absorbent wrap 700. FIG. 7A illustrates a first side view of the absorbent wrap 700, FIG. 7B illustrates a second side view of the absorbent wrap 700, FIG. 7C illustrates a top view of the absorbent wrap 700, and FIG. 7D illustrates a bottom view of the absorbent wrap 700.

Exemplary absorbent wrap 700 has a cylindrical sock or tube shape and includes a top end 702, a bottom end 704, a center portion 706, and an attachment mechanism. Top and bottom ends 702 and 704 may comprise a stretchable material, such as elastic, to maintain the absorbent wrap 700 secured to an appendage. The center portion 706 may include the same layered construction described in connection with the absorbent wrap 200, above. Specifically, the center portion 706 may include a fluid permeable inner layer, one or more layers of absorbent material, and a fluid impermeable outer layer.

The attachment mechanism may be self-attaching and selectively adjustable. For example, the attachment mechanism comprises a plurality of hook and loop material tabs 708 that are secured, at one end, to the center portion 706 of the absorbent wrap 700. Opposing ends are configured to stick to an outer surface of the center portion 706 in order to secure the absorbent wrap 700 to an appendage. In one embodiment, the plurality of hook and loop material tabs 708 may be sewn, at one end, to the center portion 706. Modifications, additions, or omissions may be made to the absorbent wrap 700 without departing from the scope of the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic a identifiers. Absent a showing that the terms "first," "second," "third," etc., connote a specific order, these terms should not be understood to connote a specific order. Furthermore, absent a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

What is claimed is:

1. A self-attaching absorbent lower leg and foot wrap comprising:
   a lower leg portion including a first wing, a first connecting strip, and a first attachment mechanism, wherein the first wing is secured at one end to the first connecting strip and the first attachment mechanism is self-attaching and selectively adjustable; and
   a foot portion including a second wing, a second connecting strip, and a second attachment mechanism, wherein the second wing is secured at one end to the second connecting strip and the second attachment mechanism is self-attaching and selectively adjustable;
   wherein:
      the first wing, the second wing, the first connecting strip, and the second connecting strip each include a layered construction comprising an absorbent material sandwiched between a fluid impermeable outer layer and a fluid permeable inner layer,
      the first and second connecting strips are connected to each other to link the lower leg portion and the foot portion together,
      the first and second wings are separated from each other such that they lack a direction connection, and
      outer surfaces of the first wing, the second wing, the first connecting strip, and the second connecting strip are made from a unitary piece of a non-woven material.

2. The self-attaching absorbent lower leg and foot wrap of claim 1, wherein the foot portion further includes a heel segment that lacks the layered construction.

3. The self-attaching absorbent lower leg and foot wrap of claim 2, wherein the heel segment includes a single layer of an elastic material.

4. The self-attaching absorbent lower leg and foot wrap of claim 1, wherein the fluid impermeable outer layer is breathable.

5. The self-attaching absorbent lower leg and foot wrap of claim 1, wherein the absorbent material includes a polymer.

6. The self-attaching absorbent lower leg and foot wrap of claim 1, wherein the first and second attachment mechanisms include hook and loop fasteners.

7. The self-attaching absorbent lower leg and foot wrap of claim 1, wherein the first and second attachment mechanisms includes an adhesive tape.

8. The self-attaching absorbent lower leg and foot wrap of claim 1, wherein the first connecting strip includes an additional layer of the absorbent material.

9. The self-attaching absorbent lower leg and foot wrap of claim 1, wherein inner surfaces of the first wing, the second wing, the first connecting strip, and the second connecting strip are all made from a unitary piece of a non-woven material.

10. The self-attaching absorbent lower leg and foot wrap of claim 1, further comprising a moisture indicator that provides a visual indication of an amount of liquid contained within the absorbent layer.

11. The self-attaching absorbent lower leg and foot wrap of claim 1, wherein the first and second wings have tapered shapes such that the first and second wings become more narrow as they move away from the first and second connecting strips.

12. A self-attaching absorbent lower leg and foot wrap comprising:
   a lower leg portion including a first wing, a first connecting strip, and a first attachment mechanism, wherein the first wing is secured at one end to the first connecting strip and the first attachment mechanism is self-attaching and selectively adjustable; and
   a foot portion including a second wing, a second connecting strip, and a second attachment mechanism, wherein the second wing is secured at one end to the second connecting strip and the second attachment mechanism is self-attaching and selectively adjustable;
   wherein:
      the first wing, the second wing, the first connecting strip, and the second connecting strip each include a layered construction comprising an absorbent material sandwiched between a fluid impermeable outer layer and a fluid permeable inner layer,
      the first and second connecting strips are connected to each other to link the lower leg portion and the foot portion together,
      the first and second wings are separated from each other such that they lack a direction connection, and
      inner surfaces of the first wing, the second wing, the first connecting strip, and the second connecting strip are all made from a unitary piece of a non-woven material.

13. The self-attaching absorbent lower leg and foot wrap of claim 12, wherein the foot portion further includes a heel segment that lacks the layered construction.

14. The self-attaching absorbent lower leg and foot wrap of claim 13, wherein the heel segment includes a single layer of an elastic material.

15. The self-attaching absorbent lower leg and foot wrap of claim 12, wherein the fluid impermeable outer layer is breathable.

16. The self-attaching absorbent lower leg and foot wrap of claim 12, wherein the absorbent material includes a polymer.

17. The self-attaching absorbent lower leg and foot wrap of claim 12, wherein the first and second attachment mechanisms include hook and loop fasteners.

18. The self-attaching absorbent lower leg and foot wrap of claim 12, wherein the first and second attachment mechanisms includes an adhesive tape.

19. The self-attaching absorbent lower leg and foot wrap of claim 12, wherein the first connecting strip includes an additional layer of the absorbent material.

20. The self-attaching absorbent lower leg and foot wrap of claim 12, further comprising a moisture indicator that provides a visual indication of an amount of liquid contained within the absorbent layer.

21. The self-attaching absorbent lower leg and foot wrap of claim 12, wherein the first and second wings have tapered shapes such that the first and second wings become more narrow as they move away from the first and second connecting strips.

22. A self-attaching absorbent lower leg and foot wrap comprising:
   a lower leg portion including a first wing, a first connecting strip, and a first attachment mechanism, wherein the first wing is secured at one end to the first connecting strip and the first attachment mechanism is self-attaching and selectively adjustable; and a foot portion including a second wing, a second connecting strip, a heel segment, and a second attachment mechanism, wherein the second wing is secured at one end to the second connecting strip and the second attachment mechanism is self-attaching and selectively adjustable;

wherein:
the first wing, the second wing, the first connecting strip, and the second connecting strip each include a layered construction comprising an absorbent material sandwiched between a fluid impermeable outer layer and a fluid permeable inner layer,
the first and second connecting strips are connected to each other to link the lower leg portion and the foot portion together,
the first and second wings are separated from each other such that they lack a direction connection, and
the heel segment lacks the layered construction and includes a single layer of an elastic material.

23. The self-attaching absorbent lower leg and foot wrap of claim 22, wherein the fluid impermeable outer layer and the fluid permeable inner layer are made from non-woven materials.

24. The self-attaching absorbent lower leg and foot wrap of claim 22, wherein the fluid impermeable outer layer is breathable.

25. The self-attaching absorbent lower leg and foot wrap of claim 24, wherein the absorbent material includes a polymer.

26. The self-attaching absorbent lower leg and foot wrap of claim 24, wherein the first and second attachment mechanisms include hook and loop fasteners.

27. The self-attaching absorbent lower leg and foot wrap of claim 24, wherein the first and second attachment mechanisms includes an adhesive tape.

28. The self-attaching absorbent lower leg and foot wrap of claim 24, wherein the first connecting strip includes an additional layer of the absorbent material.

29. The self-attaching absorbent lower leg and foot wrap of claim 24, further comprising a moisture indicator that provides a visual indication of an amount of liquid contained within the absorbent layer.

30. The self-attaching absorbent lower leg and foot wrap of claim 24, wherein the first and second wings have tapered shapes such that the first and second wings become more narrow as they move away from the first and second connecting strips.

31. A self-attaching absorbent lower leg and foot wrap comprising:
a fluid permeable inner layer that includes an inner leg wing, an inner foot wing, and an inner elongated strip constructed from a single piece of non-woven material;
a fluid impermeable outer layer that includes an outer leg wing, an outer foot wing, and an outer elongated strip constructed from a single piece of non-woven material, wherein edges of the inner layer and the outer layer are attached around their edges;
an absorbent material sandwiched between the fluid permeable inner layer and the fluid impermeable outer layer;
a first self-attaching and selectively adjustable attachment mechanism that secures the inner leg wing and outer leg wing around a leg; and
a second self-attaching and selectively adjustable attachment mechanism that is configured to secure the inner foot wing and outer foot wing around a foot.

32. The self-attaching absorbent lower leg and foot wrap of claim 31, further comprising a heel segment that lacks the layered construction.

33. The self-attaching absorbent lower leg and foot wrap of claim 32, wherein the heel segment includes a single layer of an elastic material.

34. The self-attaching absorbent lower leg and foot wrap of claim 31, wherein the absorbent material includes a polymer.

35. The self-attaching absorbent lower leg and foot wrap of claim 31, wherein the first and second self-attaching and selectively adjustable attachment mechanisms include hook and loop fasteners.

36. The self-attaching absorbent lower leg and foot wrap of claim 31, wherein the first and second self-attaching and selectively adjustable attachment mechanisms include an adhesive tape.

37. The self-attaching absorbent lower leg and foot wrap of claim 31, further comprising a moisture indicator that provides a visual indication of an amount of liquid contained within the absorbent material.

38. The self-attaching absorbent lower leg and foot wrap of claim 31, wherein:
the inner leg wing and the inner foot wing have tapered shapes such that the inner leg wing and the inner foot wing become more narrow as they move away from the inner elongated strip; and
the outer leg wing and the outer foot wing have tapered shapes such that the outer leg wing and the outer foot wing become more narrow as they move away from the outer elongated strip.

\* \* \* \* \*